US011911213B2

United States Patent
Lorraine et al.

(10) Patent No.: US 11,911,213 B2
(45) Date of Patent: Feb. 27, 2024

(54) TECHNIQUES FOR DETERMINING ULTRASOUND PROBE MOTION

(71) Applicant: General Electric Company, Schenectady, NY (US)

(72) Inventors: Peter William Lorraine, Schenectady, NY (US); David Andrew Shoudy, Niskayuna, NY (US); Asha Singanamalli, Glenville, NY (US)

(73) Assignee: General Electric Company, Schenectady, NY (US)

( * ) Notice: Subject to any disclaimer, the term of this patent is extended or adjusted under 35 U.S.C. 154(b) by 817 days.

(21) Appl. No.: 16/430,108

(22) Filed: Jun. 3, 2019

(65) Prior Publication Data

US 2020/0375571 A1 Dec. 3, 2020

(51) Int. Cl.
*A61B 8/00* (2006.01)
*G06T 7/33* (2017.01)
*G06T 7/73* (2017.01)
*A61B 8/08* (2006.01)
*G06T 7/254* (2017.01)

(52) U.S. Cl.
CPC .......... *A61B 8/4254* (2013.01); *A61B 8/4245* (2013.01); *A61B 8/5246* (2013.01); *G06T 7/254* (2017.01); *G06T 7/337* (2017.01); *G06T 7/74* (2017.01); *G06T 2207/10132* (2013.01); *G06T 2207/20224* (2013.01); *G06T 2207/30004* (2013.01)

(58) Field of Classification Search
CPC ... A61B 8/4245; A61B 8/5246; A61B 8/4254; G06T 7/254; G06T 7/74; G06T 7/337; G06T 2207/10132; G06T 2207/20224; G06T 2207/30004
See application file for complete search history.

(56) References Cited

U.S. PATENT DOCUMENTS

| | | | |
|---|---|---|---|
| 5,645,077 A * | 7/1997 | Foxlin | A61B 5/1114 600/595 |
| 5,876,342 A | 3/1999 | Chen et al. | |
| 5,899,861 A * | 5/1999 | Friemel | G01S 7/5205 600/443 |
| 6,012,458 A | 1/2000 | Mo et al. | |
| 6,095,976 A * | 8/2000 | Nachtomy | G01S 7/52046 600/443 |

(Continued)

FOREIGN PATENT DOCUMENTS

WO 2018002004 A1 1/2018

OTHER PUBLICATIONS

Krupa, Alexandre, et al.; "Full Motion Tracking in Ultrasound Using Image Speckle Information and Visual Servoing", Proceedings 2007 IEEE International Conference on Robotics and Automation, Roma, pp. 2458-2464, Apr. 10-14, 2007.

(Continued)

*Primary Examiner* — Chao Sheng

(57) ABSTRACT

The present disclosure relates to extraction of probe motion estimates from acquired ultrasound image frames. Such image-extracted probe motion data can be used alone or in combination with sensed motion data, such as acquired using an inertial measurement unit (IMU). In certain implementations, the image-extracted probe motion can be used to provide or maintain anatomic context in a sequence of images or to provide guidance to a user.

20 Claims, 20 Drawing Sheets

(56) References Cited

U.S. PATENT DOCUMENTS

| | | |
|---|---|---|
| 8,699,765 B2 | 4/2014 | Hao et al. |
| 9,561,019 B2 | 2/2017 | Mihailescu et al. |
| 9,642,572 B2 | 5/2017 | Mahfouz et al. |
| 2006/0100518 A1 | 5/2006 | Krishnan |
| 2008/0175453 A1* | 7/2008 | Hao ................. G06T 7/0012 382/128 |
| 2008/0187193 A1* | 8/2008 | Hoctor ............. G06V 30/142 382/128 |
| 2008/0306382 A1* | 12/2008 | Guracar ........... G01S 15/8995 600/437 |
| 2014/0100452 A1* | 4/2014 | Jain .................. A61B 8/486 600/424 |
| 2015/0002538 A1* | 1/2015 | Sohn ................ A61B 8/5223 345/629 |
| 2015/0005637 A1 | 1/2015 | Stegman et al. |

OTHER PUBLICATIONS

Zhang, Miaomiao, et al.; "Speckle Decorrelation of Motion in Ultrasound Fourier Images", 2014 IEEE International Ultrasonics Symposium, pp. 1203-1206, Sep. 2014.

\* cited by examiner

TECHNIQUES FOR DETERMINING ULTRASOUND PROBE MOTION

BACKGROUND

The subject matter disclosed herein relates to deriving estimates of motion of an ultrasound probe.

An ultrasound imaging system typically includes an ultrasound probe that is applied to a patient's body and a workstation or monitor that is operably coupled to the ultrasound probe. The ultrasound probe may be controlled by an operator of the ultrasound imaging system and is configured to transmit and receive ultrasound signals that are processed into an ultrasound image by the workstation or monitor. The operator positions the ultrasound probe to acquire a target anatomy or region of interest (e.g., a desired tissue or body region to be imaged) in a target scan plane. For example, by viewing real-time images of the acquired ultrasound data on the monitor or a separate display of the ultrasound imaging system, the operator may adjust the ultrasound probe into an appropriate position for imaging the target scan plane of the target region of interest.

In practice, relating the movement of the ultrasound probe to the displayed images to understand the underlying three-dimensional structure being imaged is part of the training and mental processes of the technician. Correspondingly, it may be difficult for an inexperienced technical or an untrained individual to track anatomic structures of interest from image frame to image frame and/or to fully synthesize a three-dimensional understanding of the anatomy undergoing imaging.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a method for estimating motion of an ultrasound probe is provided. In accordance with this embodiment, a sequence of ultrasound images is acquired while moving the ultrasound probe relative to an imaged volume. For ultrasound images acquired at different time intervals, one or more estimates of motion of the ultrasound probe are extracted from the respective changes across the ultrasound images. The one or more estimates of motion are used to localize a current probe position with respect to the other images in the sequence and internal anatomy of a patient.

In a further embodiment, a method for processing a sequence of ultrasound images is provided. In accordance with this embodiment, a sequence of ultrasound images is acquired while moving an ultrasound probe relative to an imaged volume. One or more features of interest are identified in at least one image of the sequence of ultrasound images. One or more estimates of motion of the ultrasound probe are extracted from the sequence of ultrasound images. Based on the one or more estimates of motion and the one or more features of interest, ultrasound images of the sequence are analyzed or synthesized.

In another embodiment, an ultrasound imaging system is provided. In accordance with this embodiment, the ultrasound imaging system comprises: an ultrasound probe and a monitor comprising a memory and a processor. The processor is communicatively coupled to the ultrasound probe and is configured to: generate a sequence of ultrasound images from ultrasound data acquired while moving the ultrasound probe relative to an imaged volume; extract one or more estimates of motion of the ultrasound probe from the respective changes across the ultrasound images; and provide feedback to a user conveying information regarding the motion of the ultrasound probe derived using the one or more estimates of motion.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As discussed herein, the present techniques relate to extraction or estimation of ultrasound probe motion and changes in orientation from acquired image data. By way of example, two techniques described involve utilizing speckle processing (e.g., changes in the speckle pattern in successive image frames) and/or image similarity metrics in such successive image frames to extract probe motion data. The extracted motion data may be used alone or may be fused with (or otherwise used to complement) motion data extracted from other sources, such as motion sensors provided as part of the ultrasound probe. By way of example, the motion data may be used to provide contextual understanding of the image contents and/or conditional detection or tracking of anatomic features of interest. For instance, the extracted or estimated motion data may be used, in conjunction with the acquired image frames to implement semantic segmentation and/or automated understanding routines that allow an anatomic feature to be visually tracked or labeled in successive image frames, including frames in which the feature may not be readily discernible or identifiable. In this manner, the motion data may facilitate synthesis or understanding of the contents of a sequence of images by leveraging extracted probe motion so that anatomic features can be labeled or identified in images where they might otherwise be indistinguishable.

Figure 1:
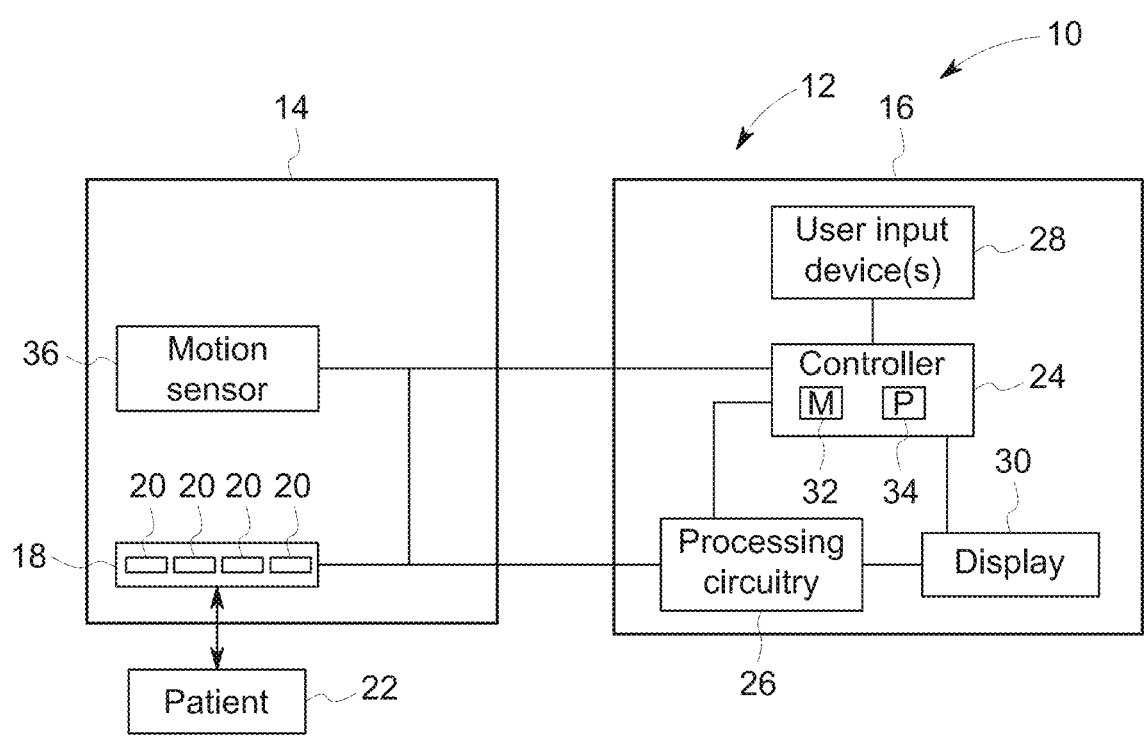
FIG. 1 is an embodiment of a block diagram of an ultrasound system, in accordance with aspects of the present disclosure.

With the preceding in mind, FIG. 1 illustrates a block diagram of an embodiment of an ultrasound imaging system 10 capable of extracting and/or utilizing motion information derived from one or more sources, including from the acquired image data itself. In the illustrated embodiment, the ultrasound system 10 is a digital acquisition and beam former system, but in other embodiments, the ultrasound system 10 may be any suitable type of ultrasound system, not limited to the illustrated type. The ultrasound system 10 may include the ultrasound probe 14 and a workstation 16 (e.g., monitor, console, user interface) which may control operation of the ultrasound probe 14 and may process image data acquired by the ultrasound probe 14. The ultrasound probe 14 may be coupled to the workstation 16 by any suitable technique for communicating image data and control signals between the ultrasound probe 14 and the workstation 16 such as a wireless, optical, coaxial, or other suitable connection.

The ultrasound probe 14 contacts the patient during an ultrasound examination. The ultrasound probe 14 may include a patient facing or contacting surface that includes a transducer array 18 having a plurality of transducer elements 20 capable of operating in a switched manner between transmit and receive modes. Each individual transducer element 20 may be capable of converting electrical energy into mechanical energy for transmission and mechanical energy into electrical energy for receiving. It should be noted that the transducer array 18 may be configured as a two-way transducer capable of transmitting ultrasound waves into and receiving such energy from a subject or patient 22 during operation when the ultrasound probe 14 is placed in contact with the patient 22. More specifically, the transducer elements 20 may convert electrical energy from the ultrasound probe 14 into ultrasound waves (e.g., ultrasound energy, acoustic waves) and transmit the ultrasound waves into the patient 22. The ultrasound waves may be reflected back toward the transducer array 18, such as from tissue of the patient 22, and the transducer elements 20 may convert the ultrasound energy received from the patient 22 (reflected signals or echoes) into electrical signals for transmission and processing by the ultrasound probe 14 and the workstation 16 to provide an ultrasound image that may be analyzed. The number of transducer elements 20 in the transducer array 18 and the frequencies at which the transducer elements 20 operate may vary depending on the application.

As previously discussed, the ultrasound probe 14 is communicatively coupled to the workstation 16 of the ultrasound imaging system 10 to facilitate image collection and processing. As will be appreciated, the workstation 16 may include a number of elements to control operation of the ultrasound probe 14, facilitate placement guidance of the ultrasound probe 14, and facilitate production and/or interpretation of ultrasound images. For instance, as illustrated, the workstation 16 may include a controller 24, processing circuitry 26, one or more user input devices 28, and a display 20. In certain embodiments, the workstation 16 may include additional elements not shown in FIG. 1, such as additional data acquisition and processing controls, additional image display panels, multiple user interfaces, and so forth.

The controller 24 may include a memory 32 and a processor 34. In some embodiments, the memory 32 may include one or more tangible, non-transitory, computer-readable media that store instructions executable by the processor 34 and/or data to be processed by the processor 34. For example, the memory 32 may include random access memory (RAM), read only memory (ROM), rewritable non-volatile memory such as flash memory, hard drives, optical discs, and/or the like. Additionally, the processor 34 may include one or more general purpose microprocessors, one or more application specific processors (ASICs), one or more field programmable logic arrays (FPGAs), or any combination thereof. The controller 24 may control transmission of the ultrasound waves into the patient 22 via the transducer array 18. Additionally, the controller 24 may process acquired data to generate a sequence of ultrasound images, may extract motion data from such a sequence of images (which may or may not be fused or otherwise combined with other motion data, such as that derived from an inertial measurement unit (IMU), accelerometer(s), gyroscope(s), magnetometer(s), electromagnetic tracker(s), optical tracker(s), and so forth), and/or may derive anatomical context or other interpretative data based on one or both of the image sequence and derived motion, as discussed in greater detail below.

The processing circuitry 26 may include receiving and conversion circuitry. The processing circuitry 26 may receive the electrical signal data from the transducer array 18 of the ultrasound probe 14 representing reflected ultrasound energy returned from tissue interfaces within the patient 22. The processing circuitry 26 may process the data from the transducer array 18, such as correcting for noise artifacts, or the like. The processing circuitry 26 may then convert the signal data into an ultrasound image for presentation via the display 30. The controller 24 may cause display of the ultrasound image or images (or a construct or model generated based on such images or raw image data) produced by the processing circuitry 26 from the signal data received from the transducer array 18 of the ultrasound probe 14.

In operation, the controller 24 may receive a signal indicative of a target anatomy of the patient 22 and/or a target scan plane of the target anatomy via the one or more user input devices 28 of the workstation 16. The one or more user input devices 28 may include a keyboard, a touchscreen, a mouse, buttons, switches, or other devices suitable to allow the operator to input the target anatomy and/or the desired scan plane of the target anatomy. Based on the target anatomy and/or the target scan plane of the target anatomy, the controller 24 may output a signal to the transducer array 18 of the ultrasound probe 14 indicative of an instruction to convert the electrical energy from the ultrasound probe 14 into ultrasound waves and transmit the ultrasound waves into the patient 22 and to detect the ultrasound energy that is reflected back from the tissue interfaces within the patient 22.

The ultrasound imaging probe 14 may additionally include a motion sensor 36, such as an IMU, which may generate data indicate of relative motion of the probe over time. In one embodiment, such an IMU may use a combination of accelerometers, gyroscopes, and/or magnetometers to generate measures of acceleration, angular rate, orientation, velocity, and so forth that characterize the motion over time experienced by the probe 14. Alternatively, one or more accelerometers, gyroscopes, and/or magnetometers may be provided in addition to or instead of an IMU and may function as such a motion sensor 36. Thus, in a more general sense, the motion sensor 36 may be a position sensor, an orientation sensor, such as a gyroscope, inertial tracking mechanism, electromagnetic tracking, optical tracking, or any other suitable sensor that may allow for detection of movement or motion of the ultrasound probe 14 over time. The motion sensor 36 may be communicatively coupled to the controller 24 via a wired or wireless connection and may send one or more signals to the controller 24 indicative of motion of the ultrasound probe 14 over time. The controller 24 may compare and/or fuse motion data derived from the motion sensor 36 with motion data extracted from the sequence of ultrasound images themselves, as discussed herein. In some embodiments, the controller 24 may control the transducer array 18 and the processing circuitry 26 to obtain and generate ultrasound images while the controller 24 derives motion data and/or anatomical context from the sequence of ultrasound images.

Figure 2:
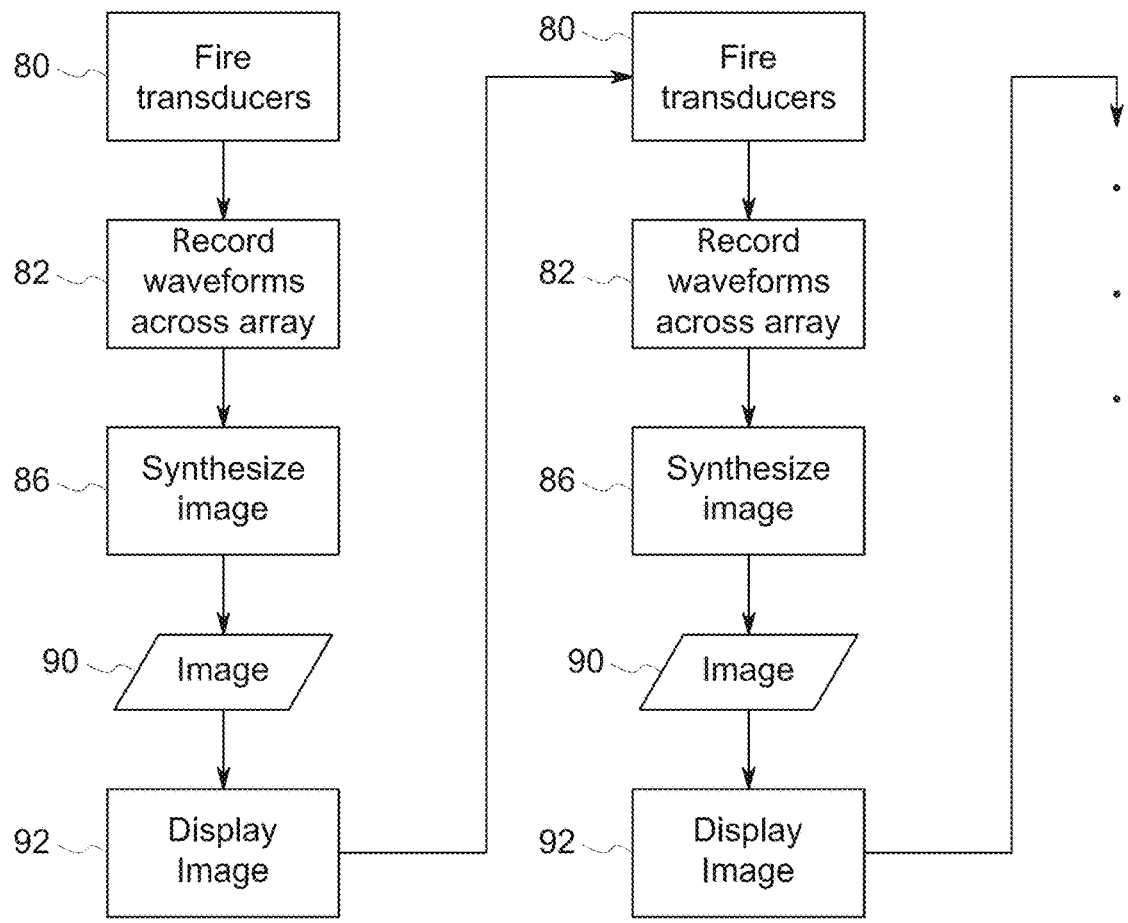
FIG. 2 depicts a conventional process flow of an ultrasound image acquisition process.

With the preceding in mind, and turning to FIG. 2, an example of a conventional approach to generating ultrasound images (such as using a system 10 as shown in FIG. 1) is illustrated. In this approach, a sonographer moves a probe 14 on a patient 22 to acquire ultrasound data of an anatomic region of interest. Such movement may comprise lateral movements of the probe 14, tilting or rotating motions of the probe 14, compression or release of the probe 14 and so forth. As part of the image acquisition, and turning to FIG. 2, the transducers 20 of the transducer array 18 may be switched between transmitting and receiving modes (denoted as firing transducers at block 80 of FIG. 2) so that ultrasound waves are generated into the tissue and the bounce back or reflection from boundary regions or layers are received at the transducers 20. The received signals may be recorded (step 82) as waveforms across the transducer array 18 and this data is used to synthesize (step 86) a two-dimensional image 90 for display (step 92). These steps may be repeated over the course of an examination (as shown in FIG. 2), with each iteration producing an image 90 of a sequence of two-dimensional images 90 over time.

A sonographer who is physically moving the probe 14 and viewing the sequence of displayed images 90 may mentally synthesize the respective views based on his movements into a three-dimensional interpretation of the imaged region, allowing the sonographer to image an organ or region of interest and to otherwise acquire the needed medical data. Such mental synthesis, however, is imprecise and highly dependent on the skill and experience of the sonographer. This subjectivity and sonographer dependence introduces a challenge in the usefulness and adoption of such ultrasound imaging techniques.

Figure 3:
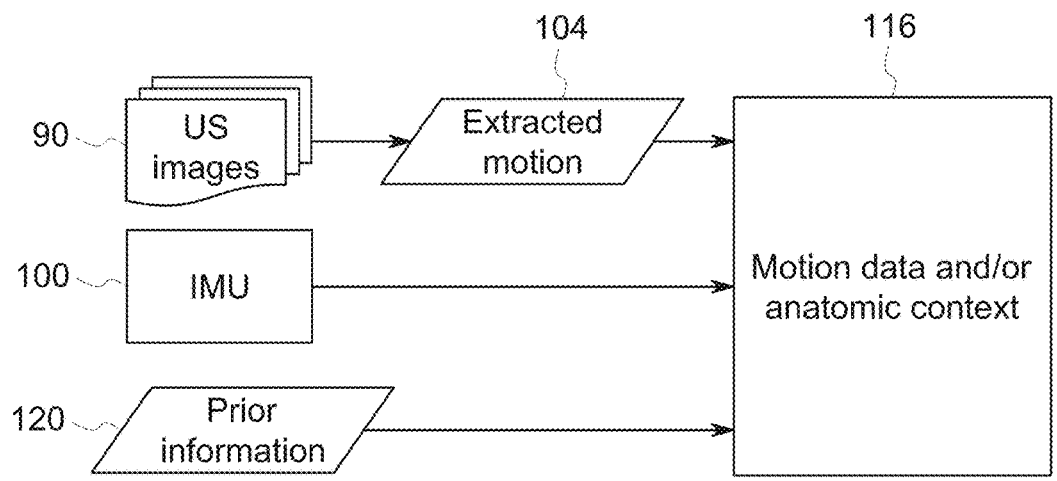
FIG. 3 depicts a current model for acquiring and utilizing motion data related to ultrasound probe motion, in accordance with aspects of the present disclosure.

With the preceding context in mind, and turning to FIG. 3, an example is provided of a present technique for extracting and using motion information during an ultrasound imaging procedure. In this example, three different types of information or data are used in the acquisition and analysis of ultrasound image data, such as to provide probe motion data (e.g., raw, corrected, or fused motion data) and/or anatomic context (e.g., labeled tissue or organs), jointly denoted by reference number 116.

A first type of motion information may be obtained from one or more IMUS 100 (or other types of motion sensors 36) that may (optionally) be present on a probe 14. As discussed herein, such an IMU 100 may use a combination of accelerometers, gyroscopes, and/or magnetometers to generate measures of acceleration, angular rate, orientation, velocity, and so forth that characterize the motion over time experienced by the probe 14. Such an IMU device may be most reliable in the presence of affirmative or active movement, but less useful in the context of small or no movements, where drift effects may introduce uncertainty into the IMU measurements. In such contexts, it may be useful to validate and/or fuse such IMU motion data, when present, with data derived by other techniques as discussed herein.

Once such technique, as illustrated on FIG. 3, is to extract motion data 104 from the sequence of acquired ultrasound images 90. By way of example, and as discussed in greater detail herein, the motion data 104 may be extracted based on changes between images 90 (e.g., difference or delta images that may be derived using two or more images, including sequential or non-sequential images), such as based on one or both of speckle processing or image similarity analysis. The images processed may be pairs or sequences of images acquired over some interval of time. Such motion extraction may be performed using machine learning routines or physics-based approaches and may be used to extract motion data for some or all of the respective six degrees of freedom in which the probe 14 may be moved (i.e., translation (in-plane and/or out-of-plane), compression, tipping, rocking, and spinning/twisting motion), which correspond to the motions that may also be measured by an IMU 100, if present, in the probe 14.

Figure 4:
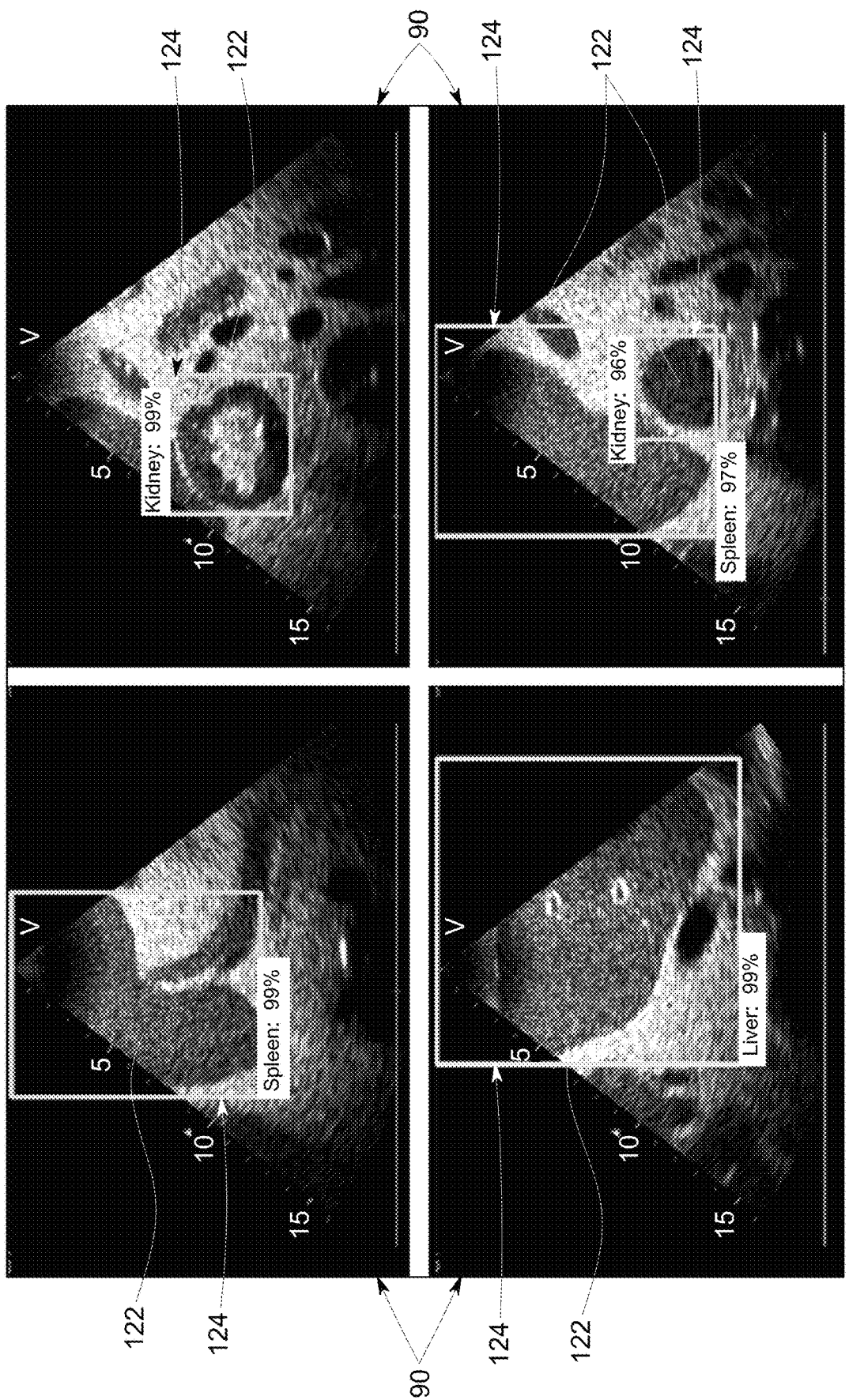
FIG. 4 depicts a set of images in which anatomic features are detected and localized using bounding boxes, in accordance with aspects of the present disclosure.

In the depicted example, prior information 120, which may be generated based on prior images 90 in the sequence, may be used to supplement the motion data and/or to provide or derive anatomic context. By way of example, prior information 120 may include identification and/or labeling of an organ, tissue, or fiducial of interest in one or more prior images 90. In one implementation an organ localization processor-implemented routine may be employed to localize and identify organs within images 90 for this purpose. For example, and turning to FIG. 4, such a neural network may be trained to detect and/or identify organs 122 (or other anatomic features of interest) within an image 90 and to draw bounding boxes 124 around identified organs or features for localization. By way of example, FIG. 4 illustrates four screenshots of ultrasound images in which such identification and localization has been performed (on a spleen, kidney, and liver) in a series of images 90.

In certain implementations semantic segmentation routines may be performed on an image or set of images to provide additional functionality. As used herein, semantic segmentation refers to labeling each pixel in an image (e.g., ultrasound image 90) as belonging to a respective class (e.g., background/foreground mask, a respective organ or anatomic feature, and so forth).

As discussed herein, once a structure has been localized and/or segmented, it can be tracked in subsequent (or preceding) image frames. Motion data, as discussed in greater detail below may be employed with such localization and/or segmentation to facilitate such tracking. For example, localization and/or segmentation information, in conjunction with the motion data derived from one or both of the ultrasound images 90 and/or IMU 100 may be used to identify or track the identified tissue, organ, or fiducial in other images where it might otherwise might not be readily identifiable. That is, position information for a feature of interest seen in one image may be retained and used with respect to a current view, in conjunction with the extracted or measured motion data, to localize or identify the same feature in the current view. In this manner, visual continuity of a region of interest may be obtained even in images where it might be difficult to discern.

The techniques illustrated schematically in FIG. 3 and described generally above may be used independent of one another or in conjunction with one another. For example, different techniques may be associated with different weaknesses and strengths, and a complementary technique, therefore, may be useful to validate measurements by another technique, and/or to combine measurements of the different techniques to improve the robustness of the measurements. By way of example, and as discussed in greater detail below, motion data extracted from ultrasound images based on image-similarity analysis (e.g., based on image-based registration techniques) may be useful to determine whether motion has occurred or not, but may be less useful to determine the scale or direction of motion. Such a validation, however, may be useful to identify motion measurements made by an IMU that are associated with drift (which may occur in low-motion contexts). In such a context, the IMU measurements that are associated with drift may be underweighted or given zero weight (or otherwise compensated for), either when taken alone or when fused or combined with other motion data.

In other examples, speckle-derived motion terms, as discussed herein, may be combined (i.e., fused) with corresponding IMU motion output, such as using extended Kalman filtering. As with motion extracted using image similarity analysis, such speckle-based motion extraction, as discussed herein, similarly has associated benefits and tradeoffs. For example, it may not be feasible to determine the polarity of motion derived from speckle processing alone. In such contexts, it may be useful to rely on a different motion data source (e.g., IMU motion data or motion data derived using other image-based techniques such as registration-based techniques) to infer directionality of the motion. Similarly, techniques employing a contextual understanding of the internal imaged anatomy may be employed to interpret how the image(s) change in response to motion in the detected degree(s)-of-freedom and to thereby infer directionality of speckle-derived motion terms.

With the preceding in mind, those scenarios in which speckle-derived motion extraction provides more reliable or robust motion measurements than an IMU (such as in low or slow motion contexts), and vice versa, may provide a more reliable motion measurement in view of the combination of the different motion measurement outputs. In addition, to the extent that a technician may employ complex motion patterns (i.e., not simply motion in one degree-of-freedom) the use of combined motion measurements acquired using different techniques may facilitate identifying or extracting such motions. For example, the combination of motion measurements derived using an IMU and the image-based motion extraction approaches discussed herein (which complement weaknesses in IMU based motion measurement) may allow identification and characterization of such complex motion.

Figure 5:
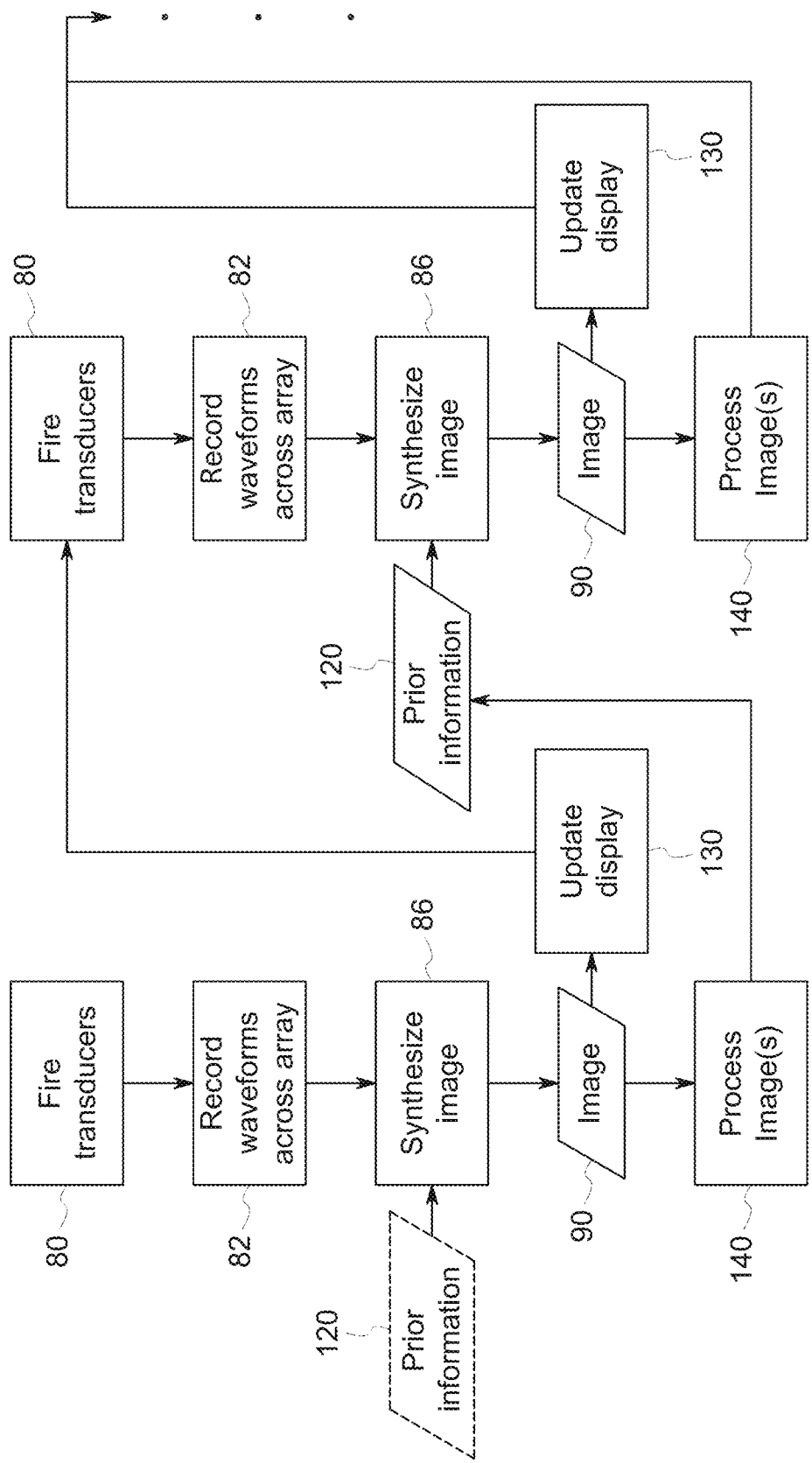
FIG. 5 depicts a process flow of an ultrasound image acquisition process, in accordance with aspects of the present disclosure.

These concepts are reflected in the process flow shown in FIG. 5. In this flow, prior information 120, if present, may be used in the image synthesis step 86, such as to facilitate or improve the synthesis step itself and/or to aid in labeling or classifying structures in the synthesized image 90. In this example, the synthesized image 90, which may include aspects derived from the prior information 120 is updated (step 130) on a display or otherwise displayed. In addition, the synthesized images 90 may be processed (step 140), such as using machine learning routines, neural networks, rule-based processing, and so forth, to generate or update prior information 102 for the next acquisition and synthesis step, as shown in FIG. 5. As discussed herein, processing (step 140) the image(s) 90 to generate the prior information 120 may involve identification and/or labeling of an organ, tissue, or fiducial of interest in one or more prior images 90 so that the structure in question can be identified and/or tracked in other images 90 (e.g., subsequent images), such as in conjunction with the IMU-based or image extracted motion data.

Figure 6:
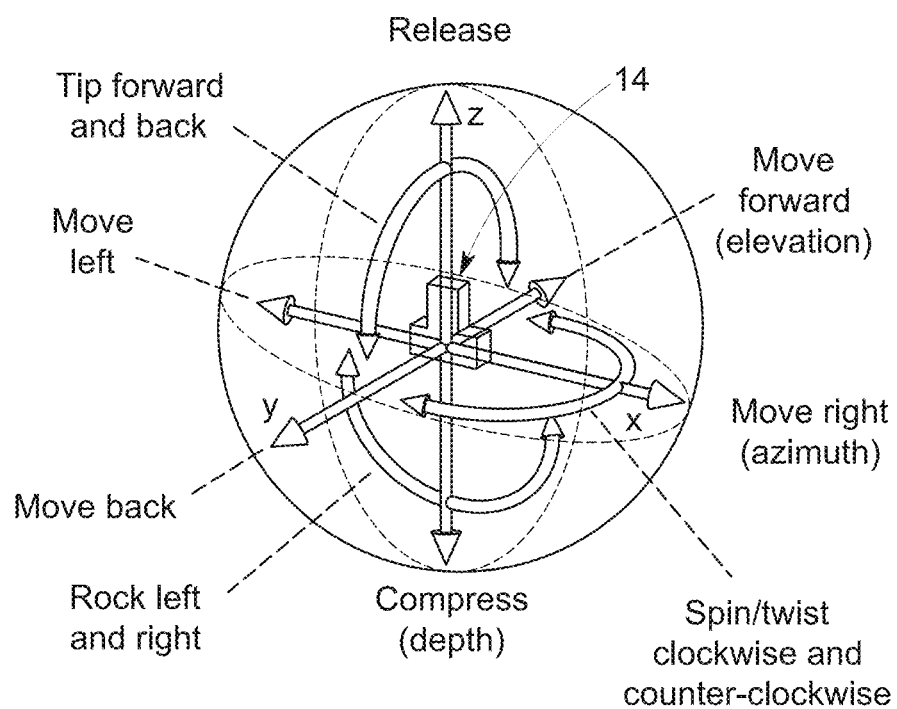
FIG. 6 depicts an ultrasound probe and associated movement axes and orientations, in accordance with aspects of the present disclosure.

To facilitate discussion related to motion of an ultrasound probe 14, FIG. 6 depicts an illustration of degrees of freedom and axes of motion with respect to an ultrasound probe, as used herein. As shown in FIG. 6, the three axes of motion (and corresponding degrees of freedom) may be denoted as elevation (e.g., moving the probe head backward and forward on the patient), azimuth (e.g., moving the probe head from left to right on the patient), compression (moving the probe head downward (compression) and upward (release) on the patient). These axes also may be used in describing three different motions related to probe head rotation or orientation with respect to the patient, which equate to three additional degrees of freedom: tipping (e.g., holding the probe head in place while moving the handle backward and forward), rocking (e.g., holding the probe head in place while moving the handle left and right), and spinning or twisting the probe (e.g., clockwise or counterclockwise rotation) about an axis of rotation generally corresponding to axis defined by the probe handle.

With this relative motion nomenclature in mind, the present approach allows for motion data extraction from the image data itself, which may or may not supplement motion data also obtained by a motion sensor, such as an IMU. As contemplated herein, motion can be extracted from image data using one or more techniques and may be extracted for some or all of the different types of motion noted above.

Figure 7:
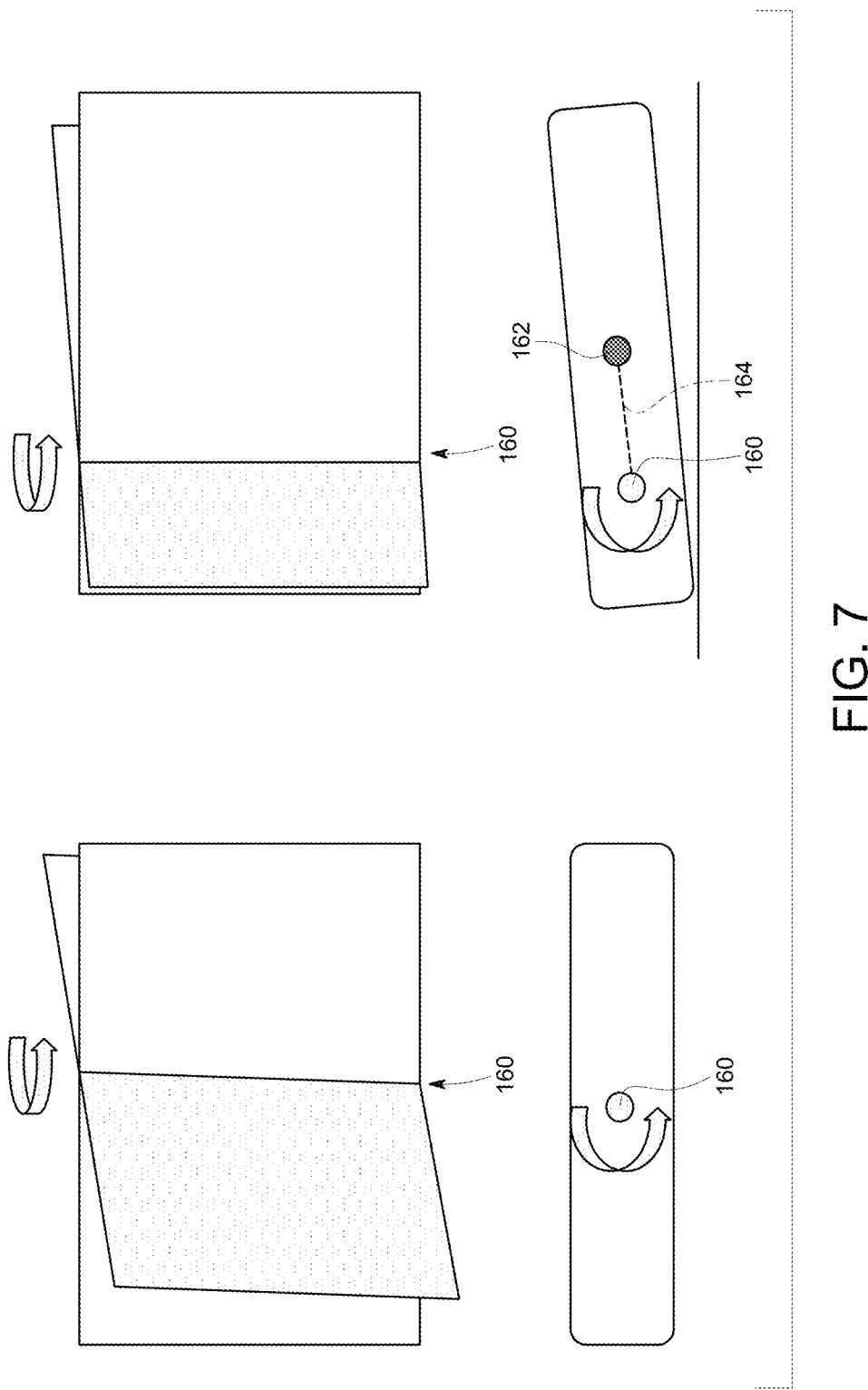
FIG. 7 depicts twisting motions that may be performed with an ultrasound probe, in accordance with aspects of the present disclosure.

For example, and turning to FIG. 7, two examples of a twist motion of a probe head relative to a patient are illustrated. On the left, an example of a twist to the probe head is illustrated that is centered about a rotation axis 160 that is centered and/or coincident with a handle axis of the probe 14. Conversely, on the right the rotation axis 160 is offset (offset distance 164) from the center 162, such as due to motion interference or other factors.

In accordance with the present techniques, motion associated with such twisting motion may be acquired from a motion sensor 36, such as an IMU 100 in which a gyroscopic sensor measures twist, or may be extracted from image data (including subtractive or difference image data generated by subtracting one image frame from another image frame (including, but not limited to a temporally adjacent or proximate image frame) or by similar difference determining processing on longer sequences of images). One example of a motion extraction based on acquired images 90 may be based on speckle processing, where speckle in an ultrasound processing context is understood to be the interference of scattered ultrasound across the coherent receiver in an ultrasound imager observed in a given image 90. Such speckle patterns are consistent or constant absent a change in position or orientation of the probe as they result from the interaction of the propagated acoustic waves with the tissue structures, which typically do not change during the course of an ultrasound imaging session. With this in mind, in the context of motion extraction for a twisting motion, speckle can be expected to change the least near the axis of rotation 160 (where motion is absent or minimal) and more the further in the image one travels from the axis of rotation 160. Thus, for a centered axis of rotation 160 speckle changes most near the edges of an image 90 and least near the center of the image 90 (the axis of rotation 160 in this example).

Figure 8:
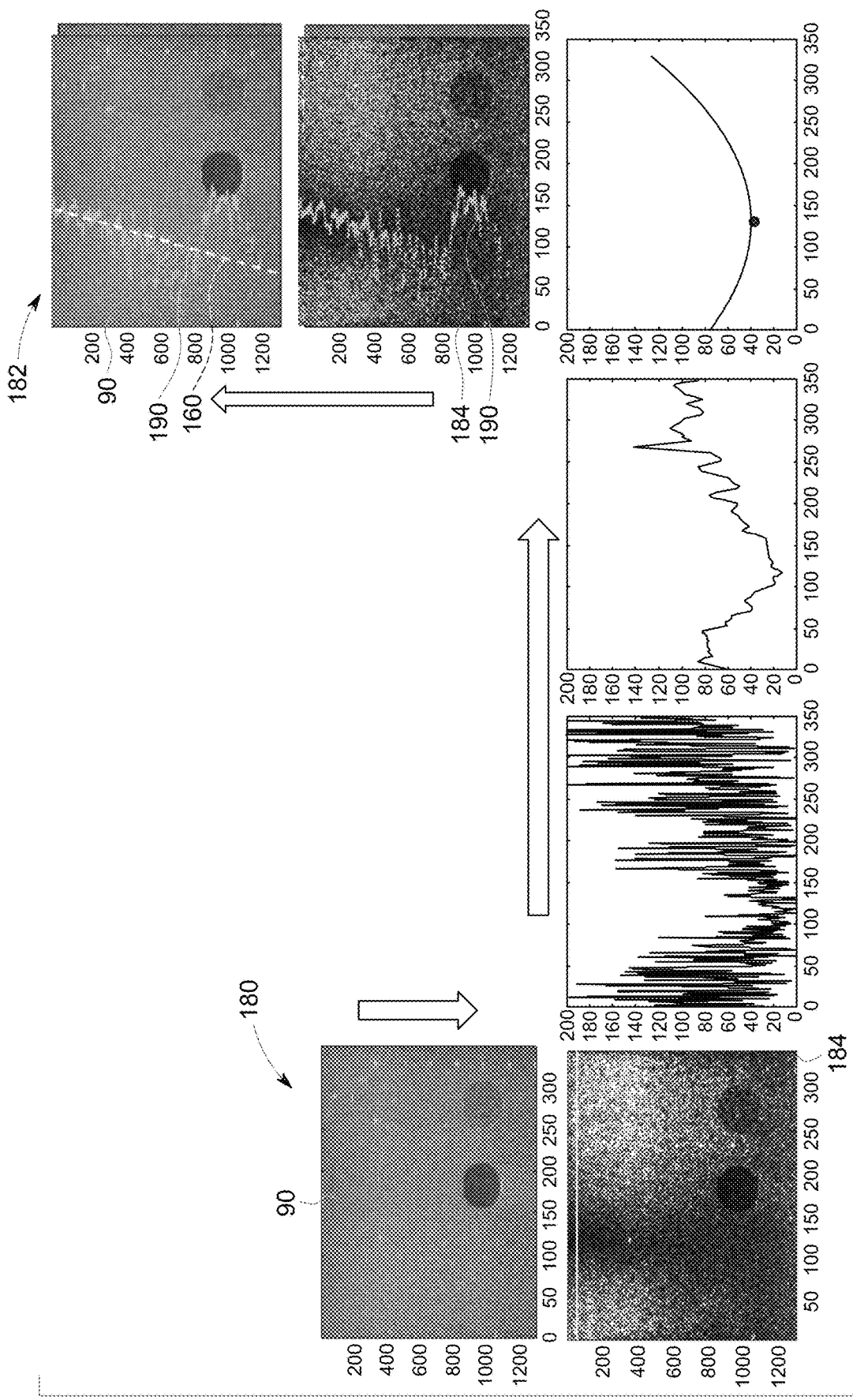
FIG. 8 depicts a visual process flow for determining twist associated with an ultrasound probe, in accordance with aspects of the present disclosure.

An example of this process is illustrated in FIG. 8 in a process chain that begins on the left at image step 180 and ends at the upper right at image step 182. In this example, the initial image, such as the most recently acquired image 90 (shown at step 180) is used to generate a difference image 184 illustrating derived differences with one or more prior images 90. In one example, the difference image is acquired by subtracting a respective first image from a second image acquired near in time to the first image (such as an adjacent sequential image frame or an image frame separated by two, three, four, etc. frames in the sequence).

In particular, in an ultrasound imager, scattered sound is detected by a coherent receiver. The beam-summed data at a given spatial location is a complex number represented by an amplitude and phase, or alternatively by an IQ pair corresponding to the real and complex amplitude. By way of example in one implementation, the pixel intensity values I for each pixel of the difference image 184 may be given by an equation like:

$$I = \mathrm{abs}(IQ(t) - IQ(t+3)) \tag{1}$$

where t represents a time corresponding to a frame in an image sequence; and IQ (t) is the complex output of the beam sum image formation algorithms. While the difference here is formed between complex image pairs, alternative approaches involving rectified or otherwise processed data may instead be employed. Based on the difference between images, pixel intensities may be measured corresponding to what is seen in the difference image 184 and these values may be fit to a statistical model (here a Gauss fit model) and smoothed (here based on a polynomial fitting function). With respect to these fit measures, a minimum may be determined (e.g., a minimum of azimuth decorrelation), with this minimum corresponding to the axis of rotation 160. Proceeding to the last two figures in the depicted process chain, the difference image 184 is shown with the observed motion 190 with respect to the axis 160 overlaid. In the final step in this chain, the respective raw image is shown with the measured axis of rotation 160 and observed motion 190 with respect to the axis 160 overlaid. In this manner, an image 90 or sequence of images 90 can be assessed for rotational, twisting motion in between images and the nature and extent of motion can be assessed and used in downstream processes, such as motion correction processes and/or tracking or labeled structures within a series of images 90.

Figure 9:
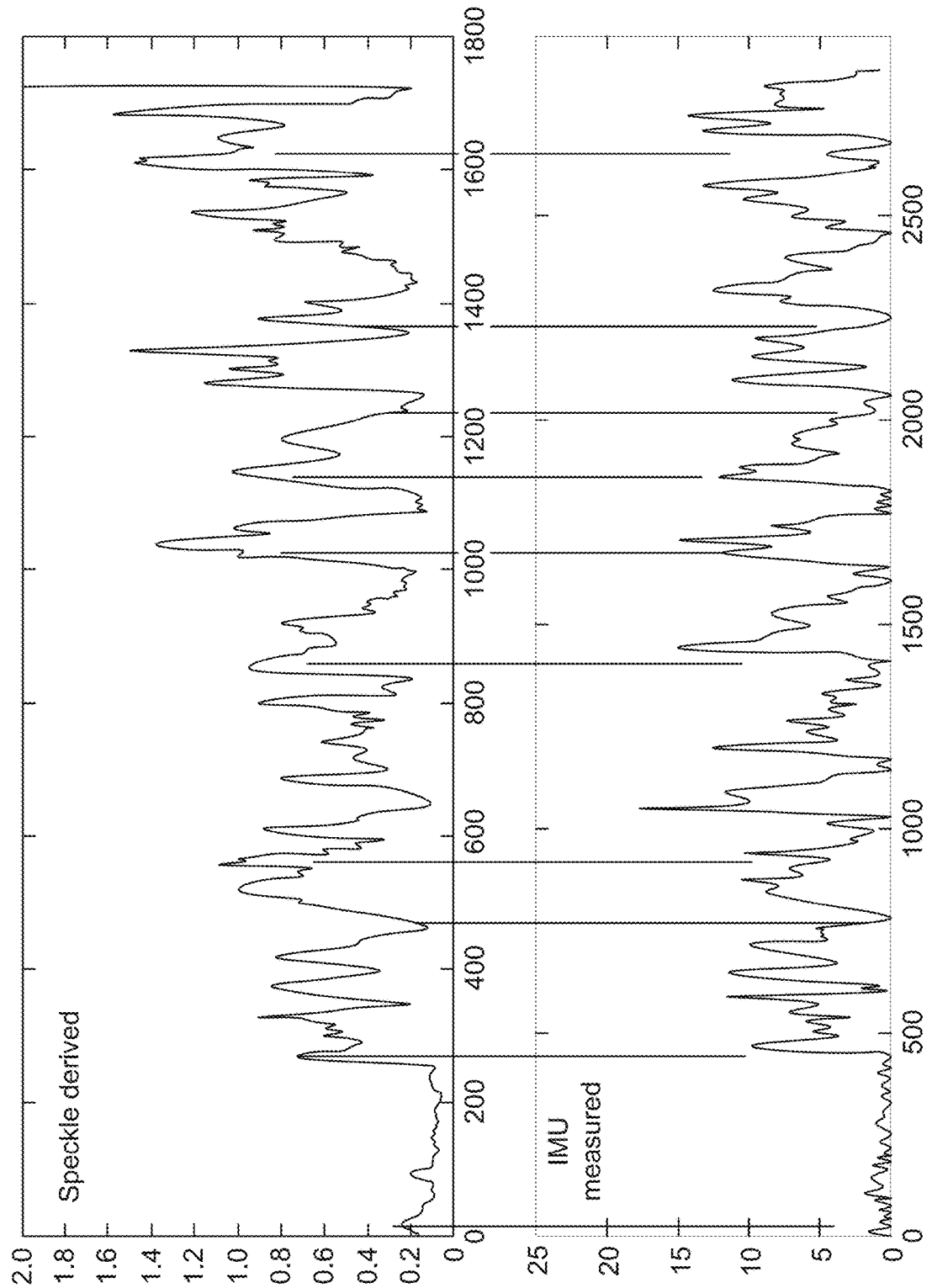
FIG. 9 depicts corresponding measures of a twist motion of an ultrasound probe head derived from image-based sources (speckle processing) and from a motion sensor, in accordance with aspects of the present disclosure.
Figure 10:
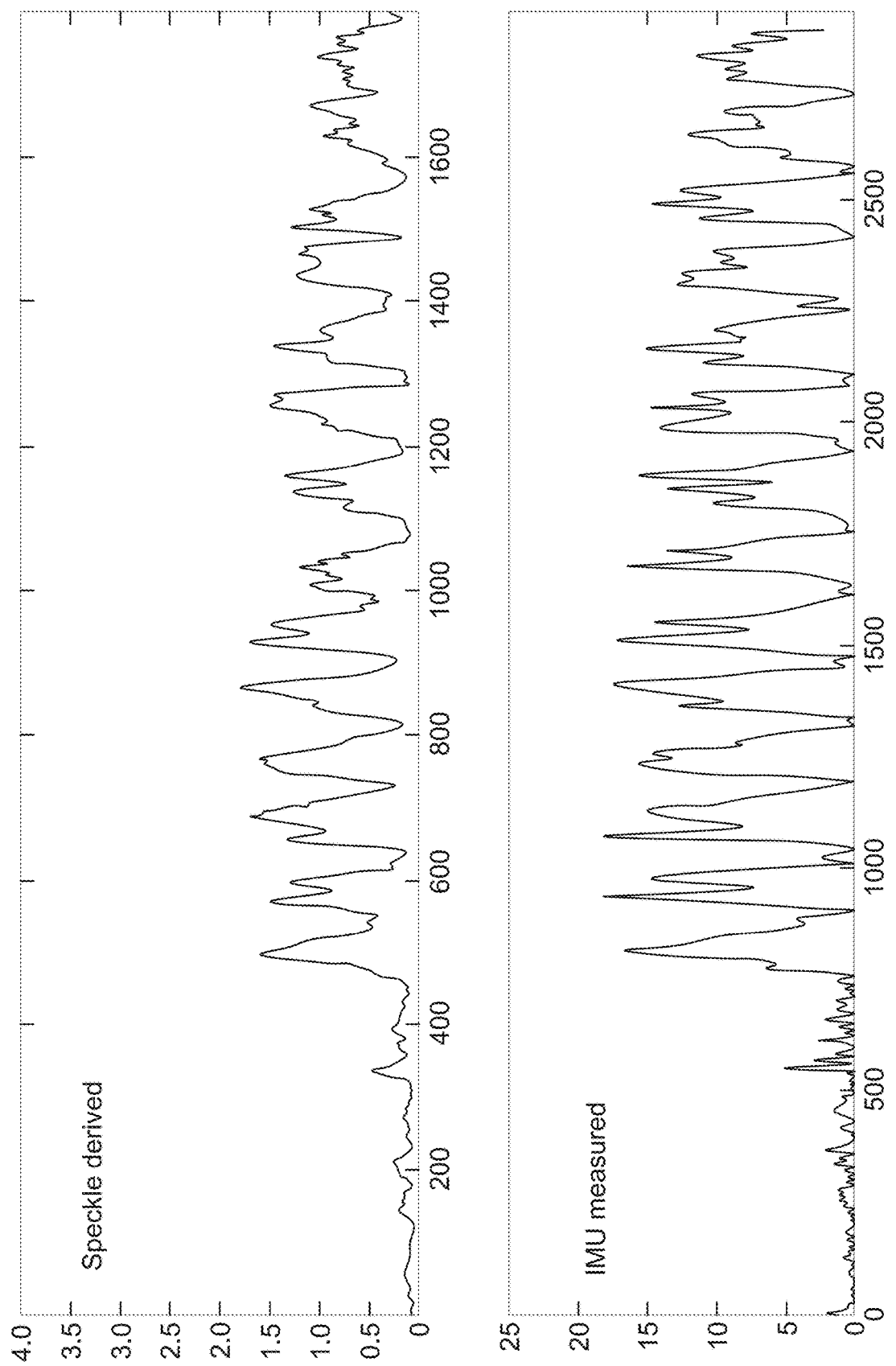
FIG. 10 depicts further corresponding measures of a twist motion of an ultrasound probe head derived from image-based sources (speckle processing) and from a motion sensor, in accordance with aspects of the present disclosure.

A validation of this approach of extracting motion data from acquired images 90 is provided in FIGS. 9 and 10. In these figures, measures of twist angle motion detection using both speckle derived rotation measurements and concurrent IMU rotation measurements (i.e., gyroscopic measurements) are shown in alignment with one another for a first data set (FIG. 9) and a second data set (FIG. 10). In FIG. 9, the depicted vertical lines are provided to illustrate the correspondence of peaks. As noted above, in these figures and similar speckle-based motion plots throughout, speckle-derived measures of motion are uni-polar (i.e., no inferred directionality), with the depicted amplitude indicating an extent or scale of motion, but not a direction. Absolute value of the IMU motion data is shown to illustrate correspondence.

In the present examples related to twist motion, data was generated by a user employing a periodic (i.e., repeated) freehand twist motion and constraining the motion to only the motion of interest (e.g., to one degree-of-freedom) to the extent possible. As shown in the figures, rotation motion (peaks) and non-rotation (valley) determined from both data sets by the two different techniques generally correspond, indicating that both techniques detected rotation motion events of the probe 14. Further, as noted above, IMU-based techniques may perform poorly with respect to slow or slight motion, while the image-based techniques either measure absolute position as with image similarity metrics or give differential motion (velocity) even at very low speeds. With this in mind, to the extent both sources of motion data may be available, the two different forms of derived twist or rotation motion may be complementary and may be used together (e.g., fused or otherwise combined) to provide improved motion information.

In a second example of twist motion extraction based on acquired images 90, twist motion may additionally or alternatively be extracted based on measures of image similarity (or changes in such measures) between images 90. By way of example, the cross-correlation between image frames 90 may provide a measure of relative offset between image frames that may be used to extract motion. In the depicted example, dashed vertical lines are indicative of the start/stop point of each repeated motion cycle.

In order to best describe motion extraction using image similarity techniques, various example plots are provided and described herein corresponding to different types of motion, and will be discussed in greater detail below. For the purpose of explanation, these plots illustrate observed motion along the z-axis (middle graph) and x-axis (bottom graph) as well as the calculated mean squared error (MSE) (top graph). In practice, the MSE may be useful as an indicator of "motion" or "no motion" (i.e., as a qualitative indicator as to whether motion is observed or not). Such qualitative indications of motion/no motion may be particularly useful to facilitate the dynamic compensation of IMU drift during periods of "no motion", such as for use in a data fusion algorithm that is based on image similarity observations, where an MSE indicative of "no motion" may allow IMU measurements attributable to drift to be zeroed out or otherwise underweighted so as not to create erroneous measures of motion based on such drift.

With respect to the z-axis (SHIFT_Z) and x-axis (SHIFT_X) plots, the depicted plots are based on image-based registration and, for the purpose of the present discussion, primarily are useful to illustrate the effects of in-plane motion (e.g., rocking, translation-azimuth, compression) and thus may provide an actual estimate of motion within this context. In such single axis motion contexts, the motion determined (i.e., estimated) based on image similarity may be proportional to what is observed or measured using an IMU. However, the effects of motion in multiple planes may be complex in terms of the depiction. However, based on observation, and as depicted in the present figures related to motion extraction using image similarity techniques, for a defined motion (or motion and anatomy) certain recognizable patterns relevant to the motion or combination of motion and anatomy may be observed and used to extract motion data.

Figure 11:
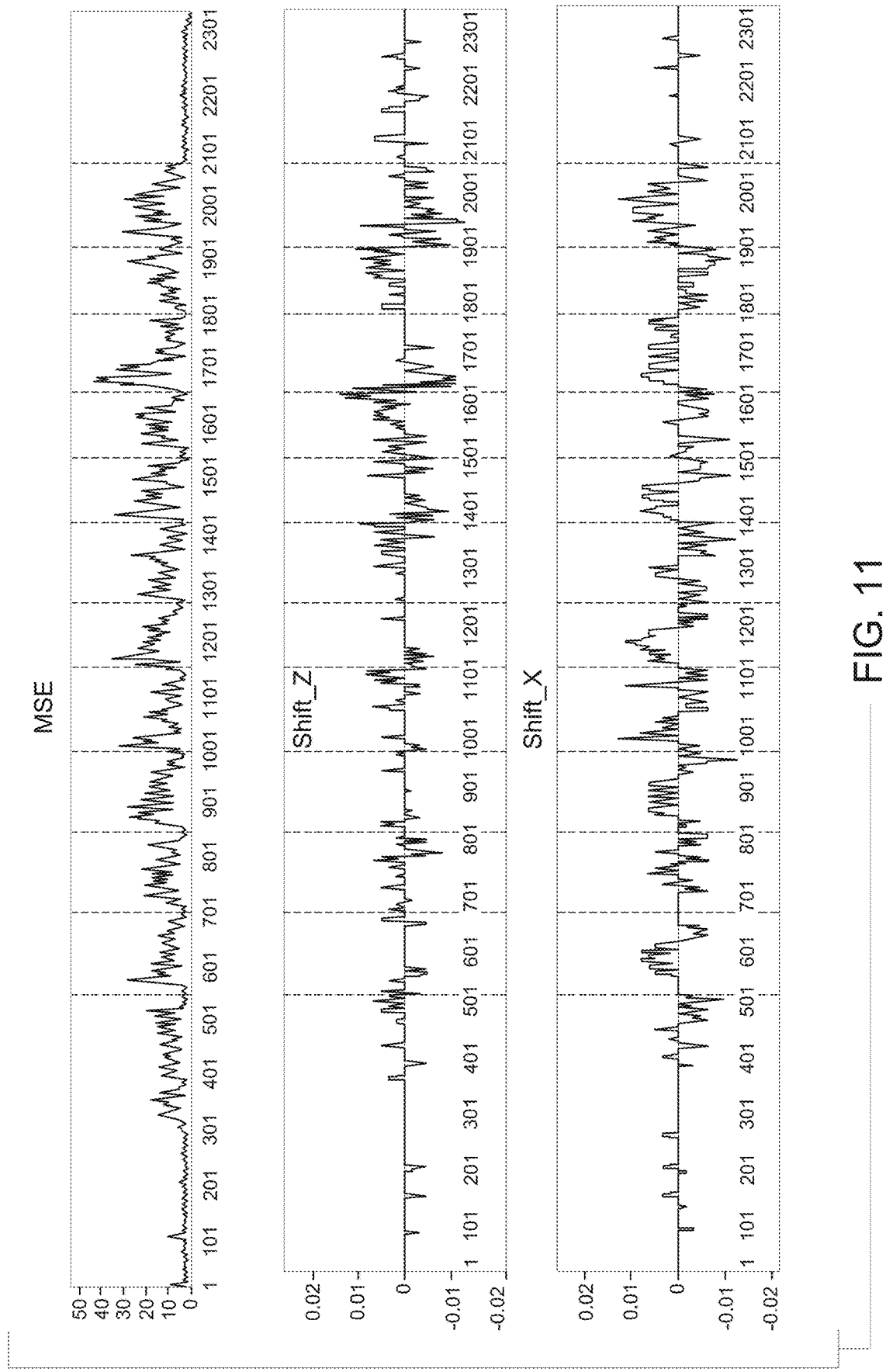
FIG. 11 depicts estimates of a twist motion of an ultrasound probe head derived from image similarity processing, in accordance with aspects of the present disclosure.

With this in mind, and turning to FIG. 11 related to a twist motion, no patterns in the SHIFT_Z or SHIFT_X plots are expected or observed since features of interest generally move out-of-plane with such a motion. However, as noted above, sometimes useful patterns that are anatomy-specific may be observed.

Figure 12:
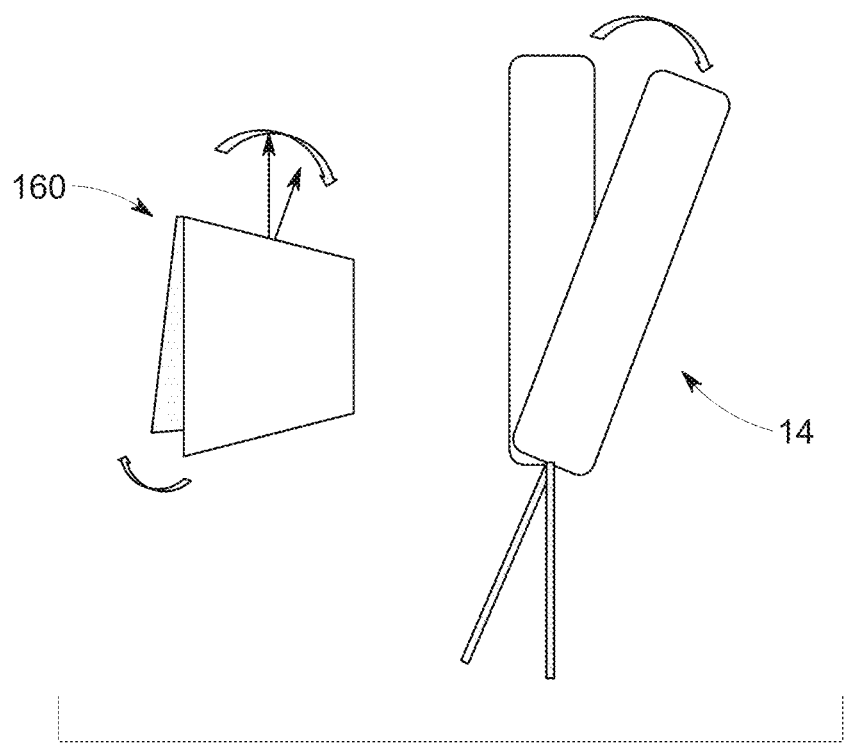
FIG. 12 depicts tipping motions that may be performed with an ultrasound probe, in accordance with aspects of the present disclosure.

While the preceding describes extraction of twist-based motion data using different image-based techniques, as described herein other motion may also be extracted using these techniques. For example, turning to FIG. 12, a tipping motion (e.g., tipping the probe handle forward and backward, such as in the elevation direction) is illustrated with respect to a probe 14.

In the present examples related to tipping motion, data was generated by a user employing a periodic (i.e., repeated) freehand tipping motion and constraining the motion to only the motion of interest (e.g., to one degree-of-freedom) to the extent possible. In accordance with the present techniques, motion associated with such tipping may be acquired from a motion sensor 36, such as an IMU 100 in which a gyroscopic sensor measures tip about an axis of rotation 160, or may be extracted from image data (including subtractive or difference image data generated by subtracting one image frame from a temporally adjacent or proximate image frame). By way of example, speckle processing as derived from difference images and as described herein may be used to measure tip motion. For example, in the context of motion extraction for a tipping motion, speckle can be expected to change the least near the axis of rotation 160 (e.g., near the patient surface, where motion is absent or minimal) and more the further one travels from the axis of rotation 160 (e.g., deeper into the patient anatomy), that is, decorrelation increases with range or distance. Thus, speckle changes most near the bottom edge of an image 90 and least near the top of the image 90 in the context of tip motion. In this manner, an image 90 or sequence of images 90 can be assessed for tipping motion between images and the nature and extent of motion can be assessed and used in downstream processes, such as motion correction processes and/or tracking or labeling structures within a series of images 90.

Figure 13:
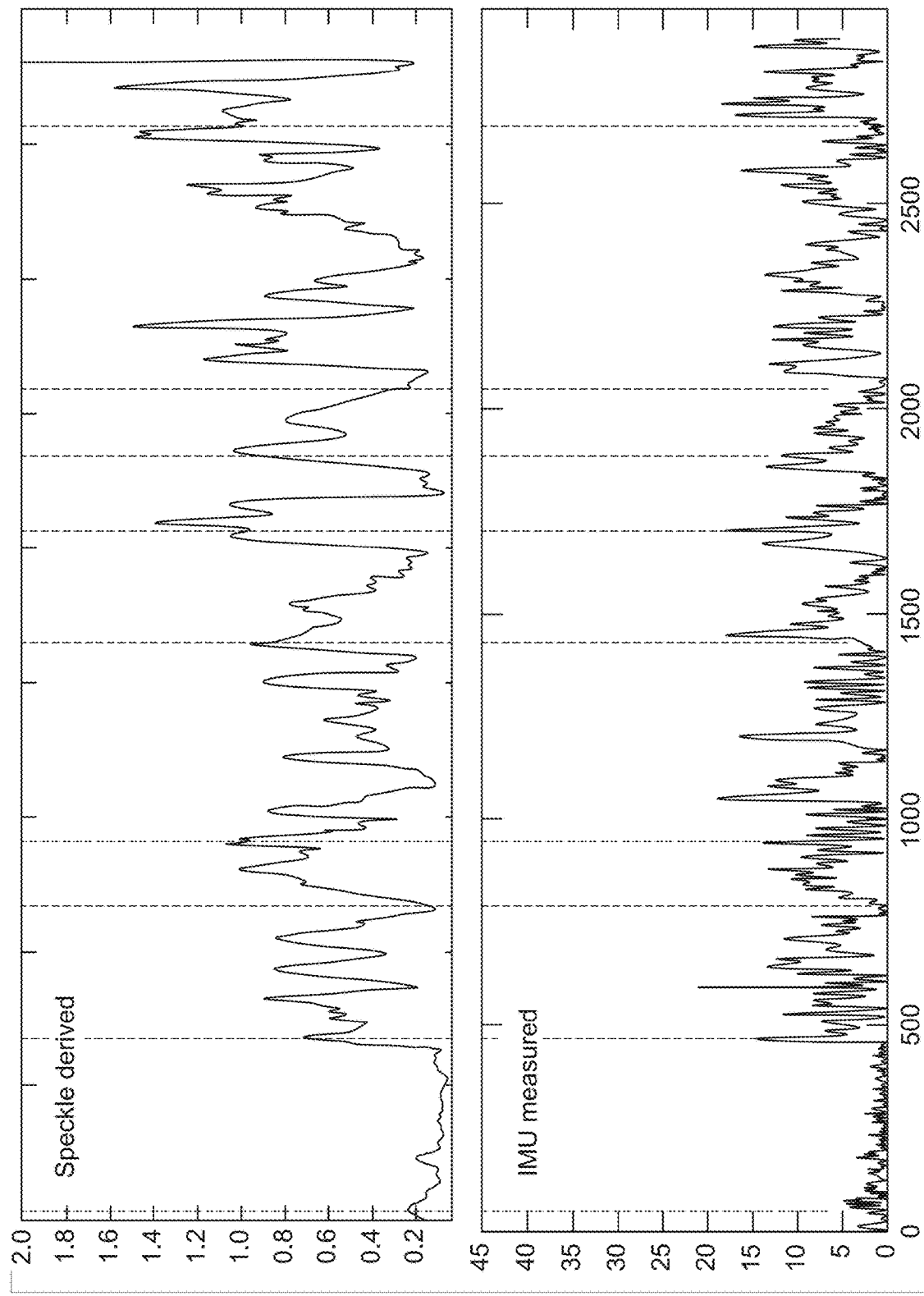
FIG. 13 depicts corresponding measures of a tipping motion of an ultrasound probe head derived from image-based sources (speckle processing) and from a motion sensor, in accordance with aspects of the present disclosure.

A validation of this approach of extracting tipping motion data from acquired images 90 is provided in FIG. 13. In this figure, measures of tip angle motion detection using both speckle derived rotation measurements and concurrent IMU rotation measurements (i.e., gyroscopic measurements) are shown in alignment with one another for a data set. In FIG. 13, the depicted vertical dashed lines are provided to illustrate the correspondence of peaks. As shown in the figures, tipping (peaks) and non-tipping (valley) events determined using the two different techniques generally correspond, indicating that both techniques detected tipping motion events of the probe 14. Further, as noted above, IMU-based techniques may perform poorly with respect to slow or slight motion, while the image-based techniques do not have the same limitation and instead reflect the extent of movement or motion, not the speed at which the movement occurred. With this in mind, to the extent both source of motion data may be available, the two different forms of derived tipping motion may be complementary and may be used together (e.g., fused or otherwise combined) to provide improved motion information.

Figure 14:
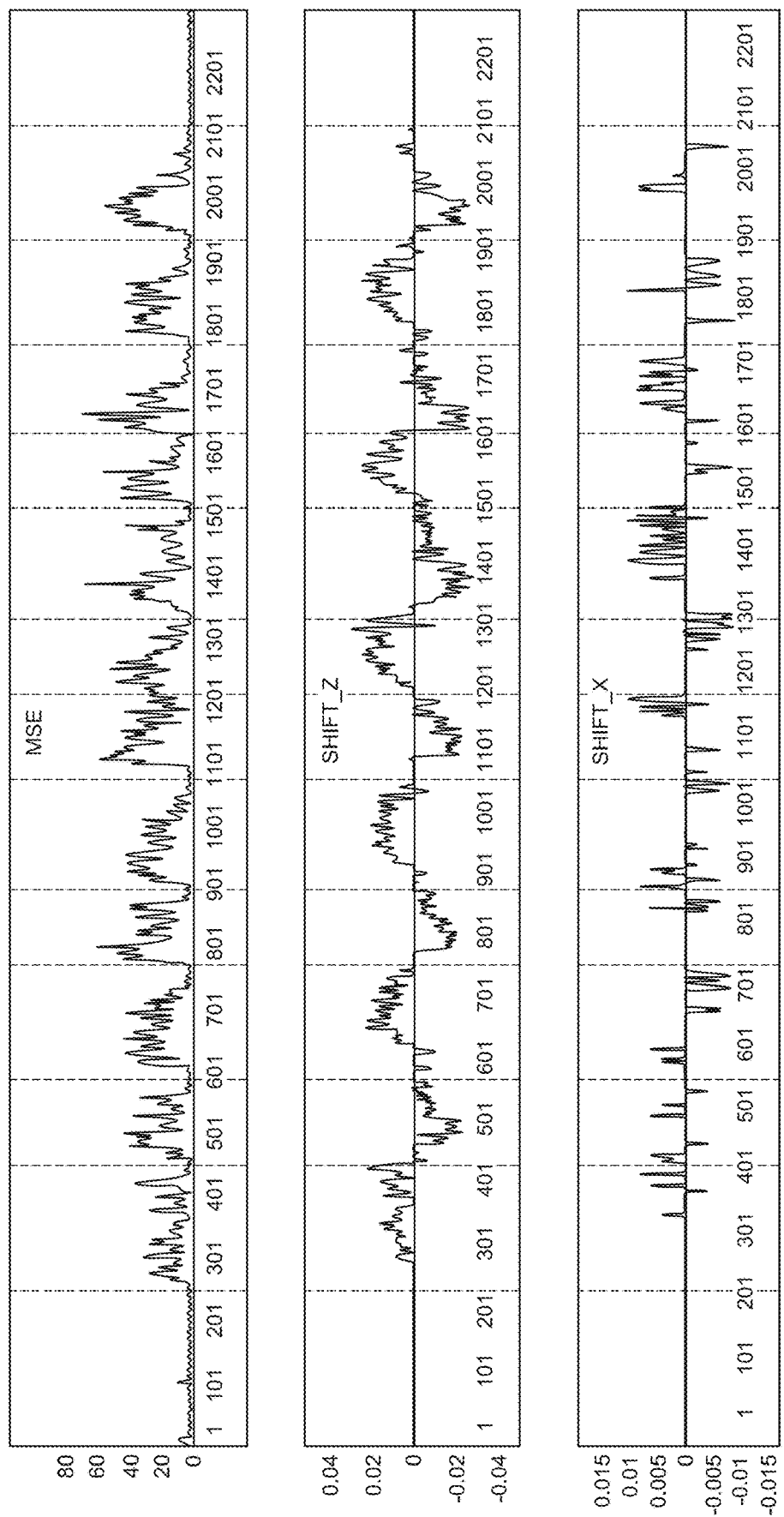
FIG. 14 depicts estimates of a tipping motion of an ultrasound probe head derived from image similarity processing, in accordance with aspects of the present disclosure.

In a second example of tip motion extraction based on acquired images 90, tip motion may be extracted or validated based on measures of image similarity (or changes in such measures) between images 90. The cross-correlation between image frames 90 may provide a measure of image similarity that may be used to extract or validate motion, which may include tip motion. In the depicted example, dashed vertical lines are indicative of the start/stop point of each repeated motion cycle. By way of example, FIG. 14 shows MSE confirmation of tip motion (tilt forward and neutral tip motion) (top graph) with the observed motion along the z-axis (middle graph) and x-axis (bottom graph). In the depicted example, a pattern corresponding to tip motion can be observed in the SHIFT_Z plot. In certain contexts, such a pattern may be anatomy dependent. For example, the observed pattern may be observed when looking at a cross section of a vessel, but may not be observed for other anatomical features. In the depicted example, no pattern is observed in the plot of SHIFT_X, though this also may be anatomy dependent.

Figure 15:
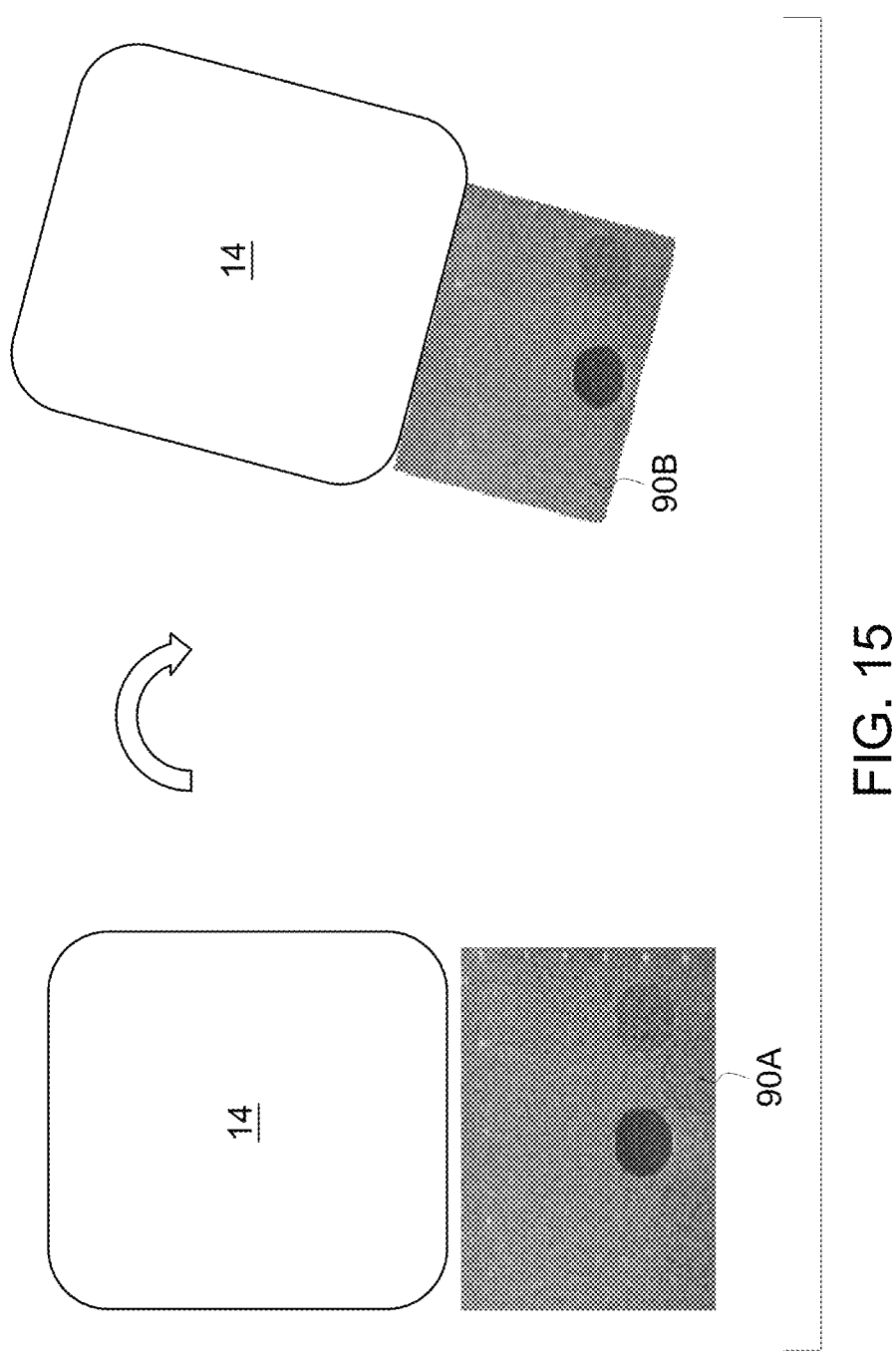
FIG. 15 depicts rocking motions that may be performed with an ultrasound probe, in accordance with aspects of the present disclosure.

As described herein other motion may also be extracted using these techniques. For example, turning to FIG. 15, a rocking motion (e.g., moving the probe handle rightward and leftward, such as in the azimuth direction, such that the rotation is about an axis normal to the image plane) is illustrated with respect to a probe 14. In the present examples related to rocking motion, data was generated by a user employing a periodic (i.e., repeated) freehand rocking motion and constraining the motion to only the motion of interest (e.g., to one degree-of-freedom) to the extent possible. In conjunction with the change in orientation to the probe 14, FIG. 15 also illustrates how such rocking motion results in relative change in position of objects within the images (90A and 90B) that remain within the field of view.

As discussed herein, motion associated with a rocking motion may be acquired from a motion sensor 36, such as an IMU 100 in which a gyroscopic sensor measures rocking about an axis of rotation 160, or may be extracted from image data (including subtractive or difference image data generated by subtracting one image frame from a temporally adjacent or proximate image frame). By way of example, speckle processing as derived from difference images and as described herein may be used to measure rocking motion.

In the context of motion extraction for a rocking motion, speckle can be expected to change the least near the axis of rotation and more the further in the image one travels from the axis of rotation, that is, decorrelation increases with range or distance. Thus, speckle changes most near the bottom edge of an image 90 and least near the top and center of the image 90 in the context of rocking motion. In this manner, an image 90 or sequence of images 90 can be assessed for rocking motion between images and the nature and extent of motion can be assessed and used in downstream processes, such as motion correction processes and/or tracking or labeled structures within a series of images 90.

Figure 16:
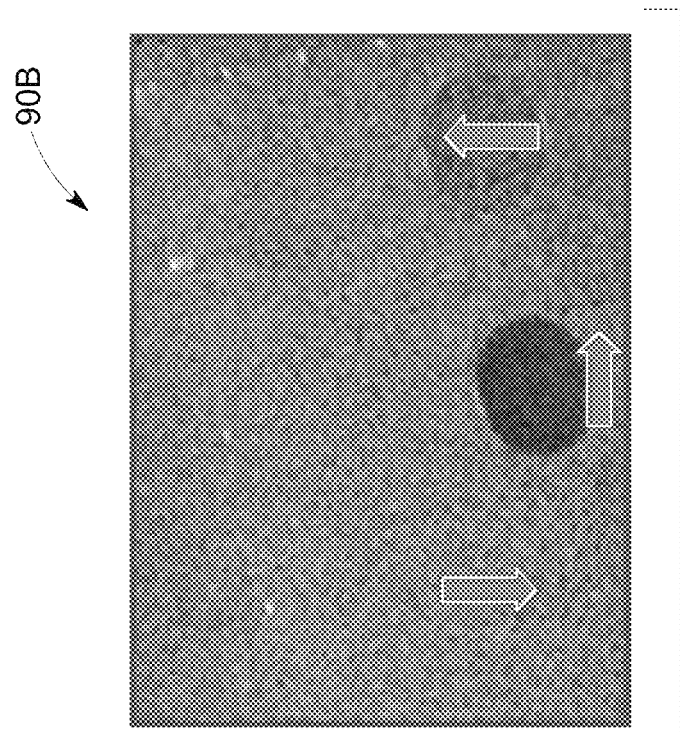
FIG. 16 depicts images acquired at different points of a rocking motion of an ultrasound probe, in accordance with aspects of the present disclosure.
Figure 16:
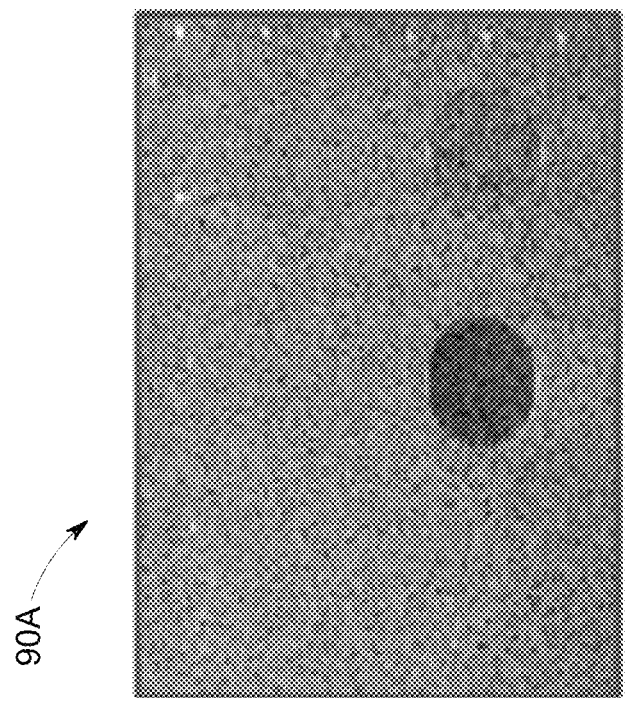
Figure 17:
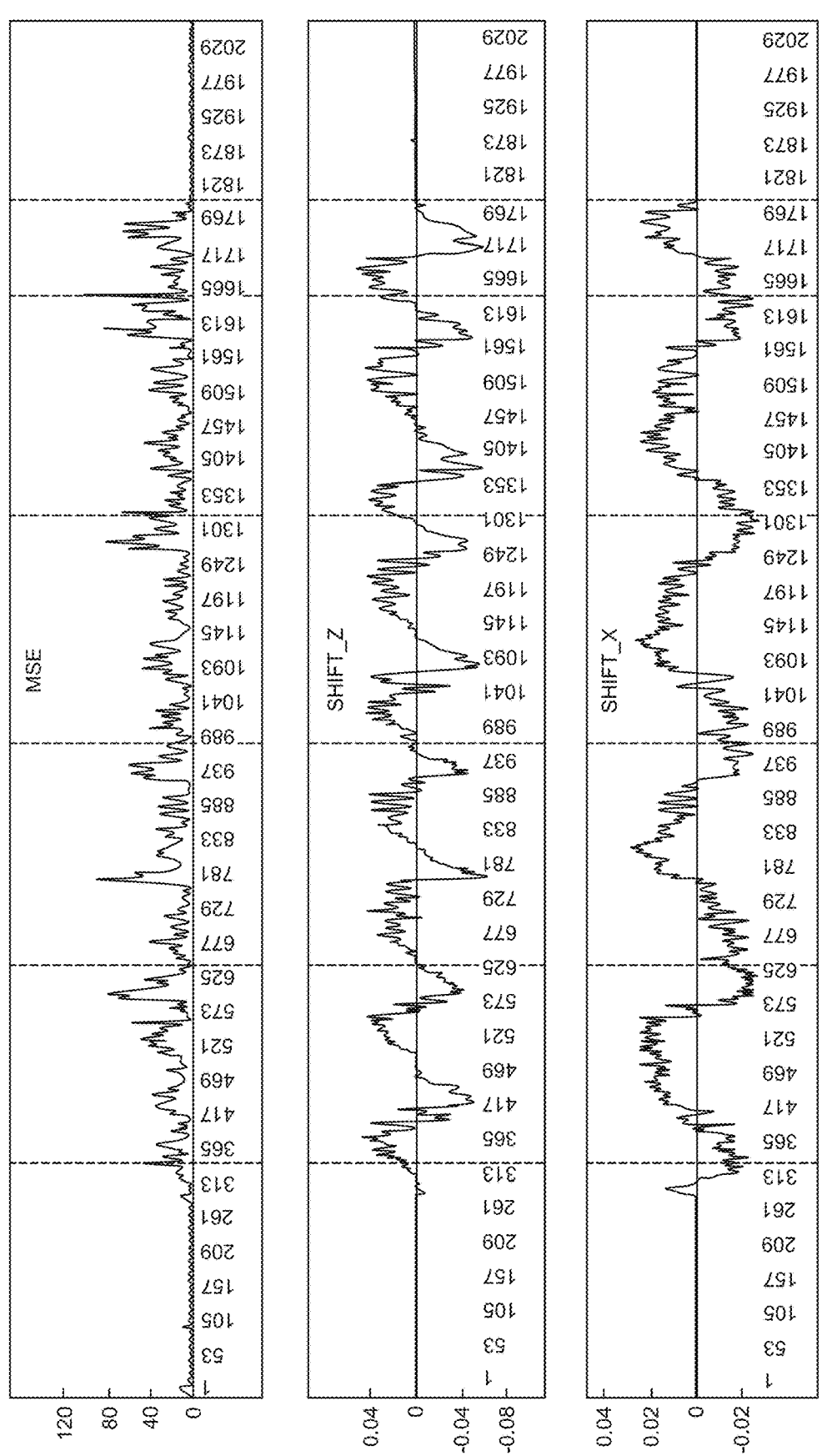
FIG. 17 depicts estimates of a rocking motion of an ultrasound probe head derived from image similarity processing, in accordance with aspects of the present disclosure.

In a second example of rocking motion extraction based on acquired images 90, and turning to FIGS. 16 and 17, rocking motion may be extracted or confirmed based on measures of image similarity (or changes in such measures) between images 90 (e.g., images 90A and 90B). As part of this process, and as shown in FIG. 16, temporally adjacent or proximate images 90 may be registered and the registration between images may be used to identify and quantify rotation of objects (as shown by directional arrows in image 90B) due to rocking of the probe 14. Turning to FIG. 17, such motion identified by an image registration process may be confirmed by MSE analysis. In the depicted example, dashed vertical lines are indicative of the start/stop point of each repeated motion cycle. Further, in this example FIG. 17 shows observable patterns in both the SHIFT_Z and SHIFT_X plots, which may be expected as an output of an image-based registration or feature extraction algorithm, where rocking motion is largely in-plane.

In addition to the probe head orientation or rotation related degrees of motion described above, non-rotational motions of the probe 14 (e.g., translation or lateral movement of the probe 14 in the x, y, or z dimensions) may also be extracted from acquired image data. For example, turning to FIG. 18, translation in the azimuth (i.e., x) dimension (i.e., in-plane) is illustrated with respect to a probe 14. In the present examples related to translation in the azimuth dimension, data was generated by a user employing a periodic (i.e., repeated) freehand motion and constraining the motion to only the motion of interest (e.g., to one degree-of-freedom) to the extent possible In accordance with the present techniques, motion associated with such translation in azimuth may be acquired from a motion sensor 36, such as an IMU 100, that measures motion along an x direction (here denoted azimuth), or may be extracted from image data (including subtractive or difference image data generated by subtracting one image frame from a temporally adjacent or proximate image frame). By way of example, speckle processing as derived from difference images and as described herein may be used to measure such translation motion.

Figure 18:
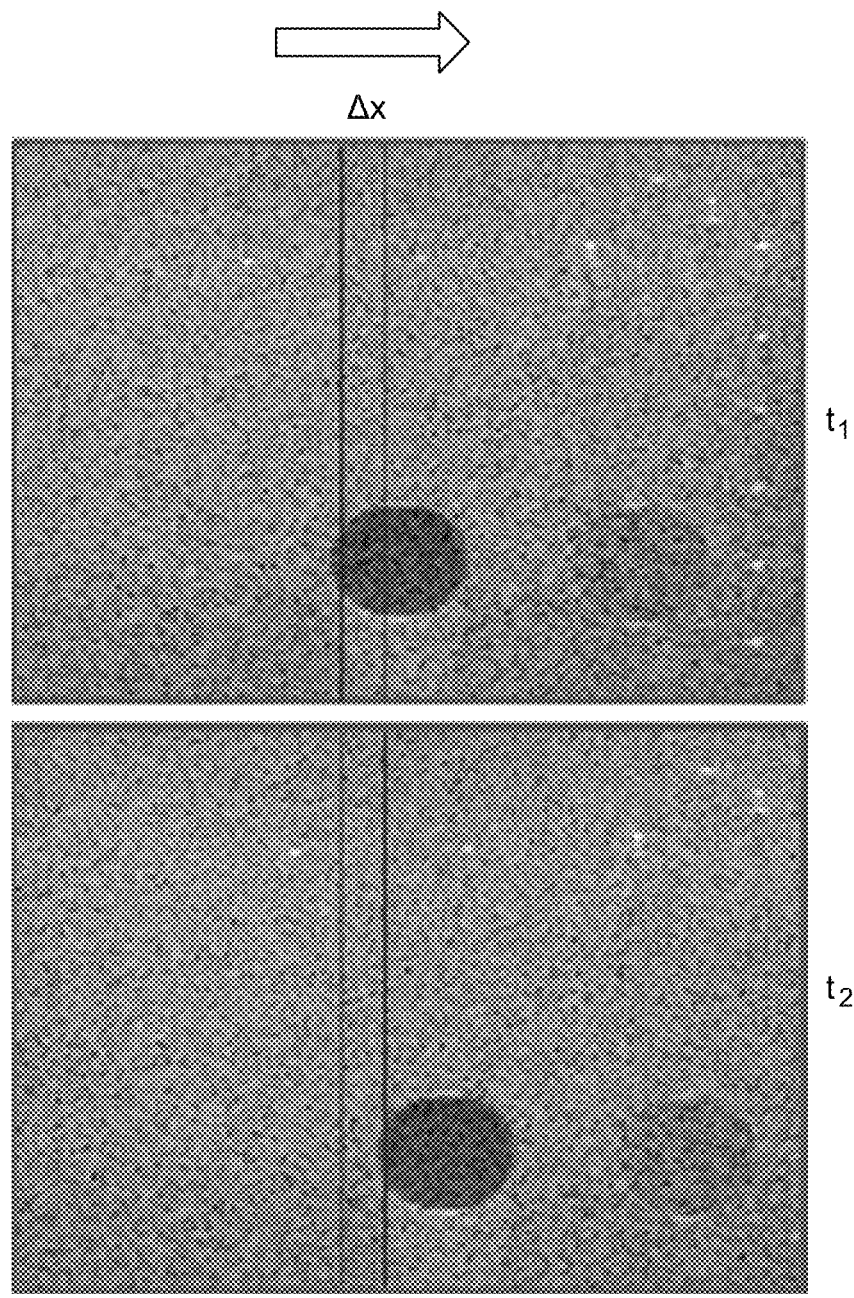
FIG. 18 depicts images acquired at different points of in-plane (azimuthal) translation motion of an ultrasound probe, in accordance with aspects of the present disclosure.

For example, in the context of motion extraction for translation motion, and turning to FIG. 18 (where probe movement is shown in the x direction over time), maximum speckle correlation between adjacent image slices (acquired at $t_1$ and $t_2$) occurs at $\Delta x$ and the change in azimuth tracks the correlation peak, with:

$$v = \Delta x / \Delta t. \tag{2}$$

In this manner, an image 90 or sequence of images 90 can be assessed for translation motion in azimuth between images and the nature and extent of motion can be assessed and used in downstream processes, such as motion correction processes and/or tracking or labeled structures within a series of images 90.

Figure 19:
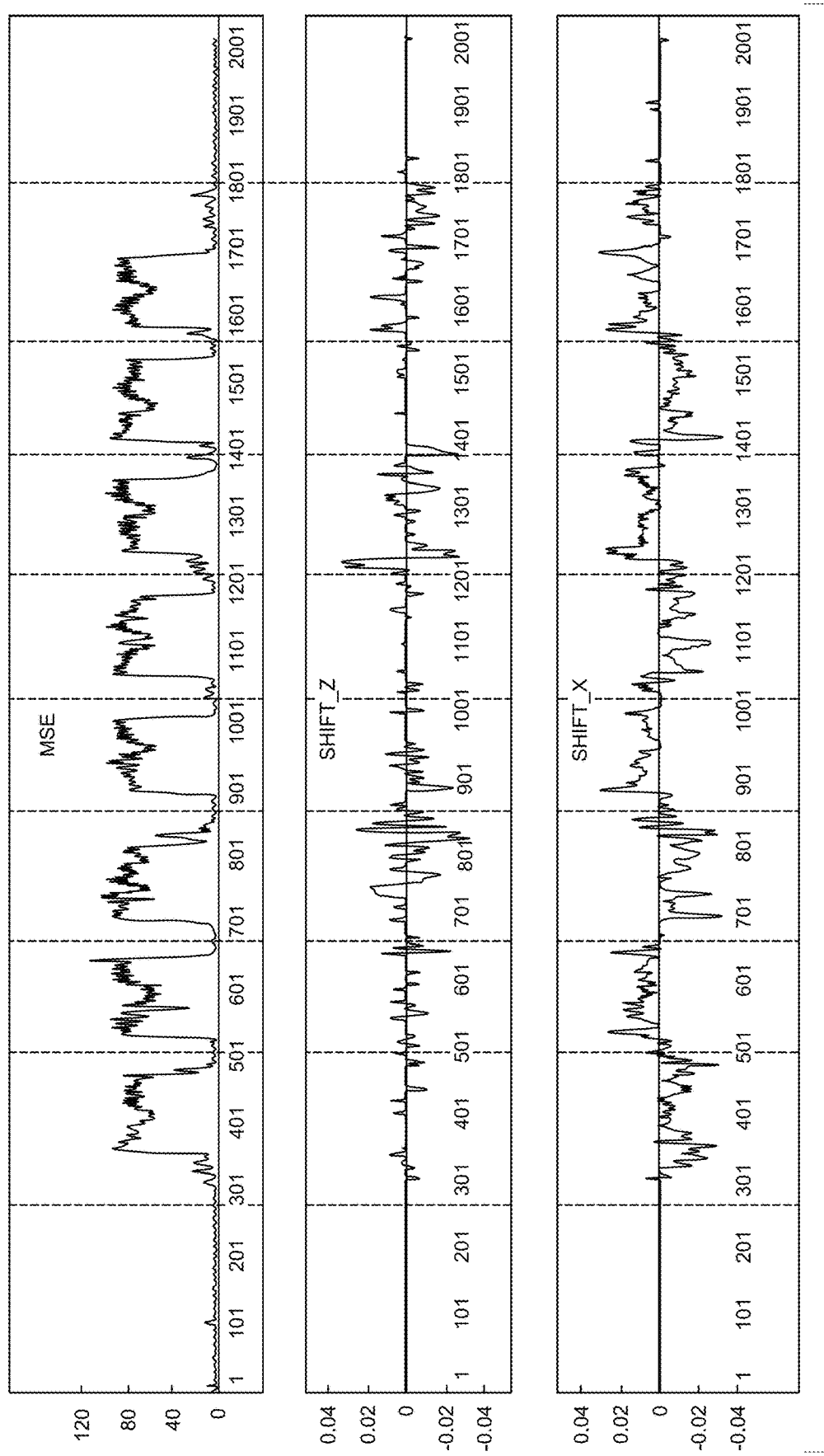
FIG. 19 depicts estimates of an in-plane (azimuthal) translation motion of an ultrasound probe head derived from image similarity processing, in accordance with aspects of the present disclosure.

In a second example of translation motion extraction based on acquired images 90, and turning to FIG. 19, translation motion may be extracted or confirmed based on measures of image similarity (or changes in such measures) between temporally adjacent or proximate image frames. As part of this process, temporally adjacent or proximate images 90 may be registered and the registration between images may be used to identify and quantify translation of the probe 14 in the azimuthal direction, such as based upon shifts in the x-plot (bottom graph, FIG. 19). As in the preceding described approaches, such motion may be confirmed or validated by MSE analysis. In the depicted example, dashed vertical lines are indicative of the start/stop point of each repeated motion cycle. Further, in this example FIG. 19 depicts valid or recognizable patterns indicative of translation motion that are observed in the SHIFT_X plot, though no significant pattern or motion is discernible in the SHIFT_Z plot.

In addition, translation in the elevation (i.e., y) dimension (i.e., out-of-plane) by the probe 14 may also be extracted from the image data. In the present examples related to translation in the elevation dimension, data was generated by a user employing a periodic (i.e., repeated) freehand motion and constraining the motion to only the motion of interest (e.g., to one degree-of-freedom) to the extent possible In accordance with the present techniques, motion associated with such translation in elevation may be acquired from a motion sensor 36, such as an IMU 100, that measures motion along a y direction (here denoted elevation), or may be extracted from image data (including subtractive or difference image data generated by subtracting one image frame from a temporally adjacent or proximate image frame). By way of example, speckle processing as derived from difference images and as described herein may be used to measure such translation motion.

For example, in the context of motion extraction for translation in elevation, speckle correlation may be determined for adjacent image frames 90. This correlation decreases uniformly across adjacent images for both azimuth and range and the rate or extent of correlation change may be used as an indication of motion in the elevation dimension. In this manner, an image 90 or sequence of images 90 can be assessed for translation motion in elevation between images and the nature and extent of motion can be assessed and used in downstream processes, such as motion correction processes and/or tracking or labeled structures within a series of images 90.

Figure 20:
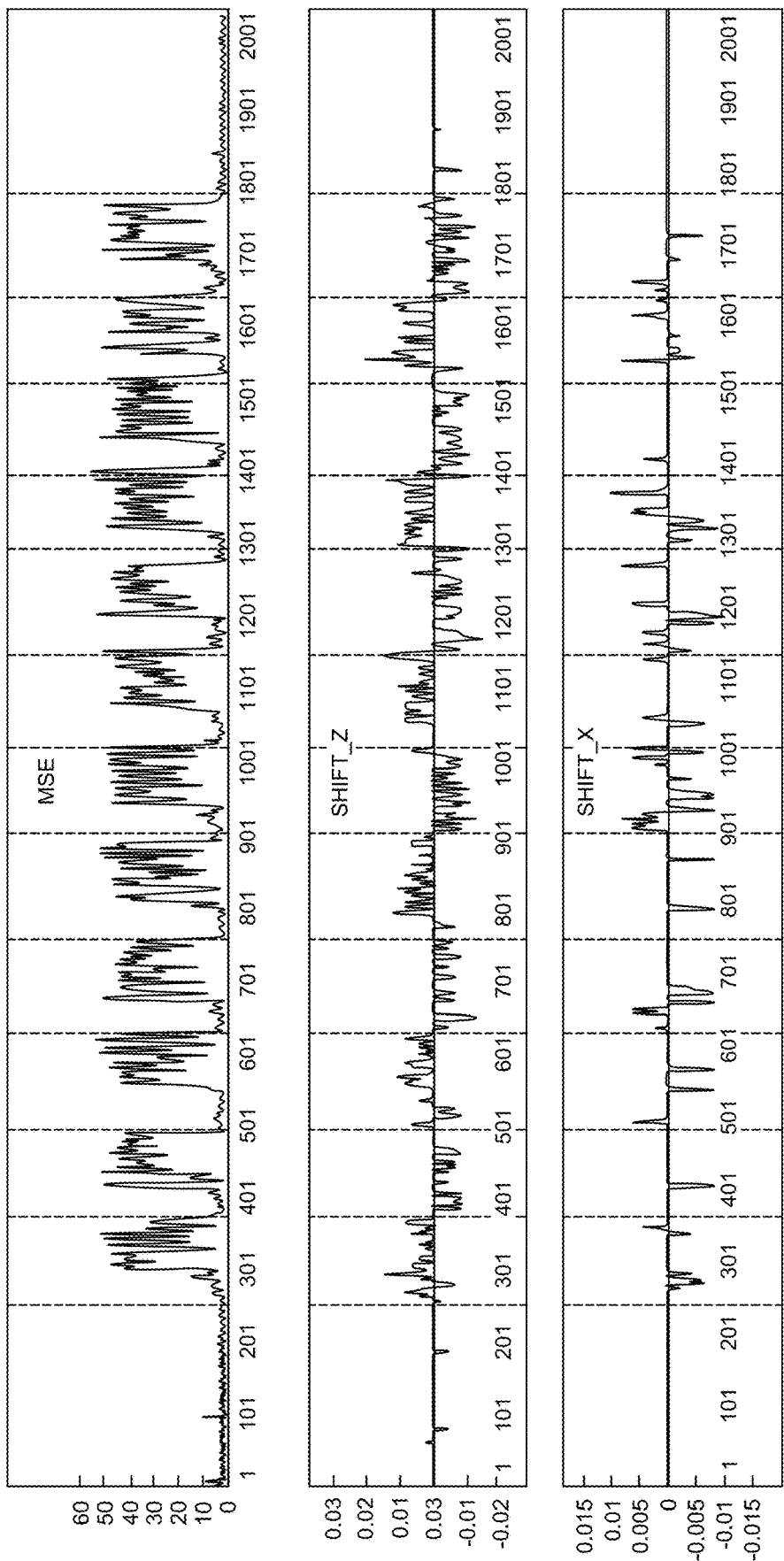
FIG. 20 depicts estimates of an out-of-plane (elevation) translation motion of an ultrasound probe head derived from image similarity processing, in accordance with aspects of the present disclosure.

In a second example of motion extraction corresponding to translation in elevation and based on acquired images 90, elevation translation motion may be extracted based on measures of image similarity (or changes in such measures) between images 90. By way of example, the cross-correlation between image frames 90 may provide a measure of image similarity that may be used to extract elevation translation motion. By way of example, FIG. 20 shows MSE confirmation or validation of motion (top graph). In the depicted example, dashed vertical lines are indicative of the start/stop point of each repeated motion cycle. With respect to the SHIFT_X and SHIFT_Z plots, any patterns observed in the elevation translation context, i.e., out-of-plane, are anatomically dependent.

Similarly, compression/release (i.e., motion in the z) dimension by the probe 14 may also be extracted from the image data. In the present examples related to compression, data was generated by a user employing a periodic (i.e., repeated) freehand compression motion and constraining the motion to only the motion of interest (e.g., to one degree-of-freedom) to the extent possible In accordance with the present techniques, motion associated with such compression or release may also be acquired from a motion sensor 36, such as an IMU 100, that measures motion along a z direction (here denoted compression (toward the patient) or release (away from the patient)), or may be extracted from image data (including subtractive or difference image data generated by subtracting one image frame from a temporally adjacent or proximate image frame). By way of example, speckle processing as derived from difference images and as described herein may be used to measure such compression or release.

For example, in the context of motion extraction for compression/release, speckle correlation may be determined for adjacent image frames 90. In the presence of compression or release there is uniform decorrelation across the image. The rate or extent of change in decorrelation may be used as an indication of compression or release motion in the z dimension. In this manner, an image 90 or sequence of images 90 can be assessed for translation motion corresponding to compression or release between images and the nature and extent of motion can be assessed and used in downstream processes, such as motion correction processes and/or tracking or labeled structures within a series of images 90.

Figure 21:
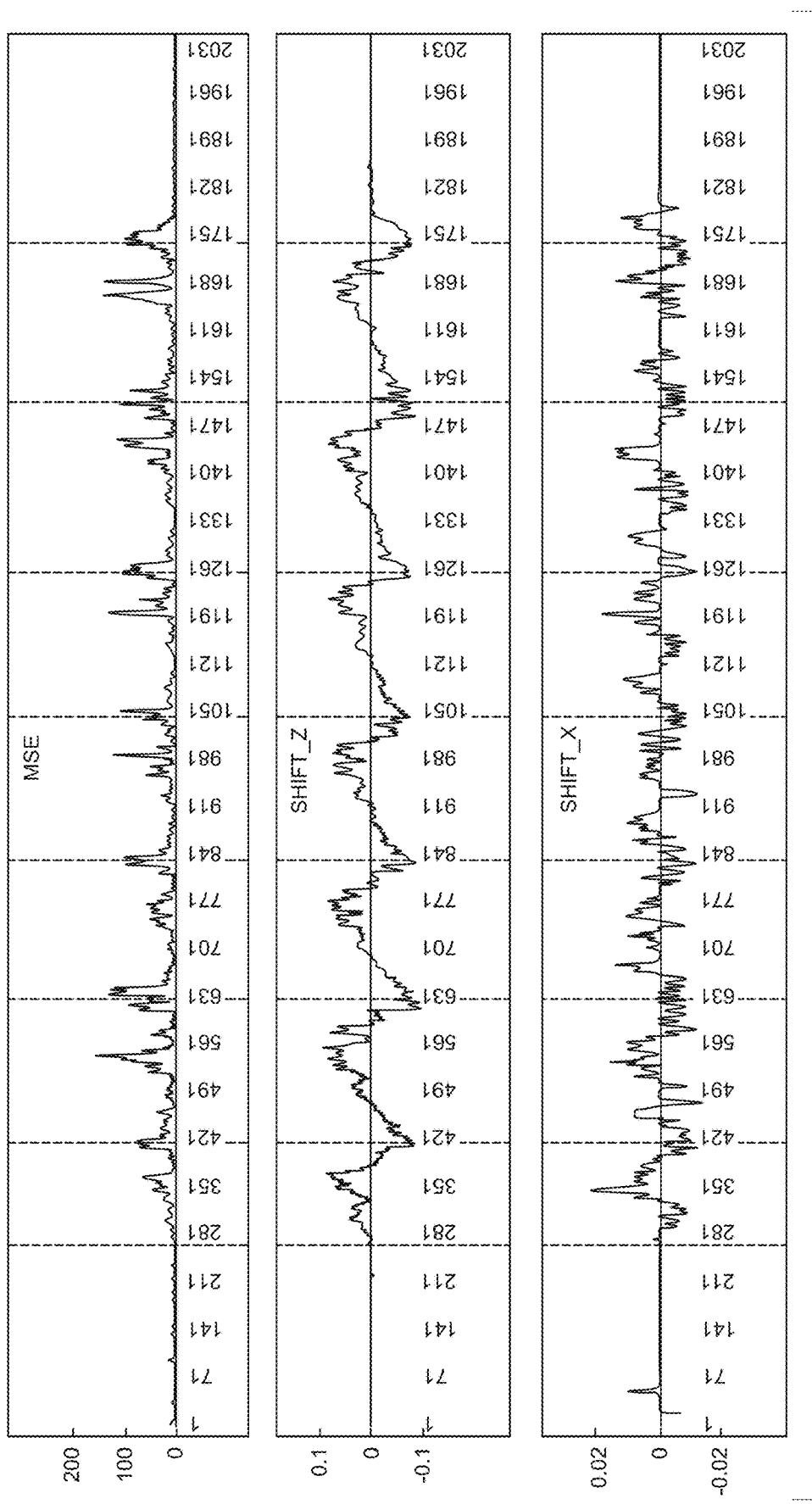
FIG. 21 depicts estimates of a compression motion of an ultrasound probe head derived from image similarity processing, in accordance with aspects of the present disclosure.

In a second example of compression/release motion extraction based on acquired images 90, and turning to FIG. 21, compression or release motion may be extracted or confirmed based on measures of image similarity (or changes in such measures) between temporally adjacent or proximate images. As part of this process, temporally adjacent or proximate images 90 may be registered and the registration between images may be used to track features as they move and squish in depth (i.e., as determined from the shift in the z-dimension), which may be used to identify and quantify translation of the probe 14 in the depth (i.e., z). As in the preceding described approaches, such motion may be confirmed or validated by MSE analysis. In the depicted example, dashed vertical lines are indicative of the start/stop point of each repeated motion cycle. In this example, FIG. 21 shows MSE confirmation of motion occurring in a depth dimension (top graph). With respect to the SHIFT_Z and SHIFT_X plots, the depicted SHIFT_Z pattern is typical of a compression motion (i.e., an in-plane motion). The SHIFT_X pattern carries little information in this instance other than possibly confirming compression if such motion results in low magnitude on SHIFT_X vs. SHIFT_Z.

Technical effects of the invention include, but are not limited to, extraction of probe motion estimates from an acquired sequence of ultrasound image frames. These estimations of motion from various ultrasound image based techniques may be combined with IMU or other tracker information in an improved hybrid estimation that provides improved performance over any single approach. The image-extracted probe motion data may, in certain implementations, be used to provide or maintain anatomic context in a sequence of images. In addition, the image-extracted probe motion data may additionally or alternatively be used to provide guidance or suggestion to a user, such as to move the probe along a trajectory, and to determine when the user has completed the motion along the trajectory.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for estimating motion of an ultrasound probe, comprising the steps of:
   acquiring a sequence of ultrasound images while moving the ultrasound probe relative to an imaged volume;
   for the ultrasound images of the sequence acquired at different time intervals, extracting motion data of the ultrasound probe from the respective changes across the ultrasound images of the sequence;
   acquiring sensed motion data from one or more motion sensors while acquiring the sequence of ultrasound images;
   localizing a current probe position with respect to the other images in the sequence and internal anatomy of a patient based on both the motion data and the sensed motion data; and
   providing feedback to a user conveying information regarding the motion of the ultrasound probe based on both the motion data and the sensed motion data, wherein the feedback comprises labeling of a feature of interest that is preserved between ultrasound images of the sequence.

2. The method of claim 1, wherein the ultrasound images of the sequence acquired at different time intervals are processed to form respective difference images from which the motion data of the ultrasound probe is extracted.

3. The method of claim 1, wherein extracting the motion data of the ultrasound probe comprises performing speckle processing on the ultrasound images of the sequence acquired at different time intervals.

4. The method of claim 1, wherein extracting the motion data of the ultrasound probe comprises using image similarity driven image registration on the ultrasound images of the sequence acquired at different time intervals.

5. The method of claim 1, wherein the one or more motion sensors comprises an electromagnetic tracker or an optical tracker within or attached to the ultrasound probe.

6. The method of claim 1, further comprising fusing the motion data and the sensed motion data to generate fused data, and wherein said localizing the current probe position comprises localizing the current probe position with respect to the other images in the sequence and internal anatomy of the patient based on the fused data.

7. The method of claim 1, wherein the providing feedback comprises displaying the labeling of the feature of interest in one or more ultrasound images of the sequence of ultrasound images where the feature of interest is not discernable.

8. The method of claim 1, wherein said localizing the current probe position with respect to the other images in the sequence and internal anatomy of a patient based on both the motion data and the sensed motion data comprises comparing the motion data to the sensed motion data.

9. The method of claim 8, wherein said comparing the motion data to the sensed motion data comprises at least one of using the motion data to validate the sensed motion data or using the sensed motion data to validate the motion data.

10. The method of claim 8, wherein said comparing the motion data to the sensed motion data comprises using the motion data to identify motion measurements in the sensed motion data that are associated with drift.

11. The method of claim 10, further comprising fusing the motion data and the sensed motion data to generate fused data, wherein the motion measurements in the sensed motion data that are associated with drift are either given zero weight or underweighted when fused with the motion data.

12. A method for processing a sequence of ultrasound images, comprising the steps of:
   acquiring the sequence of ultrasound images while moving an ultrasound probe relative to an imaged volume;
   identifying one or more features of interest in multiple ultrasound images of the sequence;
   extracting motion data of the ultrasound probe from the sequence of ultrasound images;
   acquiring sensed motion data from one or more motion sensors while acquiring the sequence of ultrasound images;
   localizing a current probe position with respect to the other images in the sequence and internal anatomy of a patient based on both the motion data and the sensed motion data; and
   providing feedback conveying information regarding the motion of the ultrasound probe based on both the motion data and the sensed motion data, wherein the feedback comprises labeling of the one or more features of interest that is preserved between ultrasound images of the sequence.

13. The method of claim 12, wherein extracting the motion data comprises performing speckle processing on difference images generated from the sequence of ultrasound images.

14. The method of claim 12, wherein extracting the motion data comprises using image similarity driven image registration techniques on the ultrasound images of the sequence acquired at different time intervals to validate or update the motion data.

15. An ultrasound imaging system, comprising:
   an ultrasound probe;
   a monitor comprising a memory and a processor, wherein the processor is communicatively coupled to the ultrasound probe and is configured to:
      generate a sequence of ultrasound images from ultrasound data acquired while the ultrasound probe is moved relative to an imaged volume;
      extract motion data of the ultrasound probe from the respective changes across the ultrasound images of the sequence; and
      provide feedback to a user conveying information regarding the motion of the ultrasound probe derived using the motion data, wherein the feedback comprises labeling of a feature of interest that is preserved between ultrasound images of the sequence based on the motion data.

16. The ultrasound imaging system of claim 15, wherein the processor is configured to extract the motion data of the ultrasound probe by performing speckle processing on difference images generated from the sequence of ultrasound images.

17. The ultrasound imaging system of claim 15, wherein the processor is configured to extract the motion data of the ultrasound probe by using image similarity driven image registration on the ultrasound images of the sequence acquired at different time intervals.

18. The ultrasound imaging system of 17, wherein the feedback comprises displaying the labeling of the feature of interest in one or more ultrasound images of the sequence of ultrasound images where the feature of interest is not discernable.

19. The ultrasound imaging system of claim 15, wherein the feedback further comprises displaying a box around the feature of interest.

20. The ultrasound imaging system of claim 19, wherein the labeling is displayed along an edge of the box.

* * * * *